(12) United States Patent
Melsheimer et al.

(10) Patent No.: US 7,892,215 B2
(45) Date of Patent: Feb. 22, 2011

(54) INSERT FOR COUPLING SHEATHS USED IN MEDICAL DEVICES

(75) Inventors: Jeffry Scott Melsheimer, Springville, IN (US); Dharmendra Pal, Wilmington, MA (US)

(73) Assignee: Cook Incorporated, Bloomington, IN (US)

( * ) Notice: Subject to any disclaimer, the term of this patent is extended or adjusted under 35 U.S.C. 154(b) by 461 days.

(21) Appl. No.: 11/408,345

(22) Filed: Apr. 20, 2006

(65) Prior Publication Data

US 2006/0282041 A1    Dec. 14, 2006

Related U.S. Application Data

(60) Provisional application No. 60/673,199, filed on Apr. 20, 2005.

(51) Int. Cl.
   *A61M 25/00*    (2006.01)
   *A61M 31/00*    (2006.01)
   *A61M 25/16*    (2006.01)
(52) U.S. Cl. .................. 604/284; 604/103.04; 604/535
(58) Field of Classification Search ......... 604/533–539, 604/523, 524, 526, 284, 528, 164.13, 264, 604/103, 103.04
   See application file for complete search history.

(56) References Cited

U.S. PATENT DOCUMENTS

| 4,580,568 | A |   | 4/1986  | Gianturco |
| 4,944,745 | A | * | 7/1990  | Sogard et al. ............... 606/194 |
| 5,035,706 | A |   | 7/1991  | Giantureo et al. |
| 5,156,594 | A | * | 10/1992 | Keith ..................... 604/103.09 |
| 5,282,824 | A |   | 2/1994  | Gianturco |
| 5,380,304 | A |   | 1/1995  | Parker |
| 5,413,557 | A | * | 5/1995  | Solar ....................... 604/103.1 |
| 5,507,732 | A | * | 4/1996  | McClure et al. ............. 604/533 |
| 5,507,771 | A |   | 4/1996  | Gianturco |
| 5,690,644 | A |   | 11/1997 | Yurek et al. |
| 5,700,253 | A |   | 12/1997 | Parker |
| 5,720,776 | A |   | 2/1998  | Chuter et al. |
| 5,743,875 | A |   | 4/1998  | Sirhan et al. |
| 5,951,508 | A | * | 9/1999  | Van Driel .................. 604/6.15 |

(Continued)

FOREIGN PATENT DOCUMENTS

EP    0 850 653 A2    7/1998

(Continued)

OTHER PUBLICATIONS

"Zilver® 518 Biliary—Stent," COOK®, 2005, 6 pgs.

(Continued)

*Primary Examiner*—Kevin C Sirmons
*Assistant Examiner*—Larry R Wilson
(74) *Attorney, Agent, or Firm*—Brinks Hofer Gilson & Lione

(57) ABSTRACT

An insert for joining sheaths for use in a medical device is described. The insert has a first end including a first operative coupling and a second end including a second operative coupling. The first operative coupling is for engaging a first tube at its distal end, and the second operative coupling is for engaging a second tube at its proximal end. The insert also includes a first passageway extending through the insert from the second end to an exit port disposed between the first operative coupling and the second operative coupling. This disclosure also provides a catheter including such an insert, and a method of assembling a catheter.

30 Claims, 8 Drawing Sheets

U.S. PATENT DOCUMENTS

| | | | |
|---|---|---|---|
| 6,063,318 A | 5/2000 | Houser et al. | |
| 6,248,092 B1 * | 6/2001 | Miraki et al. | 604/96.01 |
| 6,299,635 B1 | 10/2001 | Frantzen | |
| 6,380,457 B1 | 4/2002 | Yurek et al. | |
| 6,589,227 B2 | 7/2003 | Sønderskov Klint | |
| 6,592,549 B2 | 7/2003 | Gerdts et al. | |
| 6,613,075 B1 | 9/2003 | Healy et al. | |
| 6,676,590 B1 * | 1/2004 | Urick et al. | 600/3 |
| 6,723,071 B2 | 4/2004 | Gerdts et al. | |
| 6,743,252 B1 | 6/2004 | Bates et al. | |
| 6,755,855 B2 | 6/2004 | Yurek et al. | |
| 6,939,370 B2 | 9/2005 | Hartley et al. | |
| RE39,668 E * | 5/2007 | Bagaoisan et al. | 604/96.01 |
| 2002/0007145 A1 | 1/2002 | Stivland et al. | |
| 2003/0135198 A1 * | 7/2003 | Berhow et al. | 604/524 |
| 2004/0015150 A1 | 1/2004 | Zadno-Azizi | |
| 2004/0116833 A1 | 6/2004 | Kato et al. | |
| 2005/0171473 A1 | 8/2005 | Gerdts et al. | |
| 2006/0020321 A1 | 1/2006 | Parker | |
| 2006/0155357 A1 | 7/2006 | Melsheimer | |
| 2006/0190069 A1 | 8/2006 | Baker-Janis et al. | |

FOREIGN PATENT DOCUMENTS

| | | |
|---|---|---|
| EP | 1 004 327 A1 | 5/2000 |

OTHER PUBLICATIONS

PCT Notification of Transmittal of the International Search Report and the Written Opinion of the International Searching Authority, or the Declaration dated Aug. 30, 2006 for International Patent Application No. PCT/US2006/015149, 10 pgs.

* cited by examiner

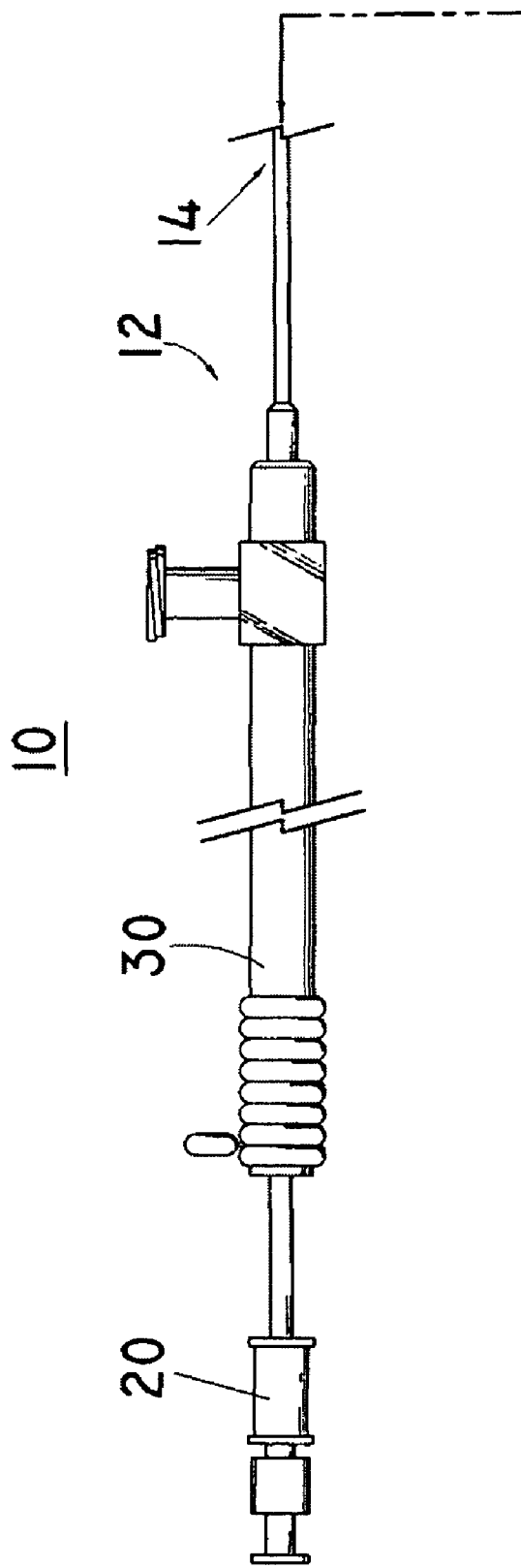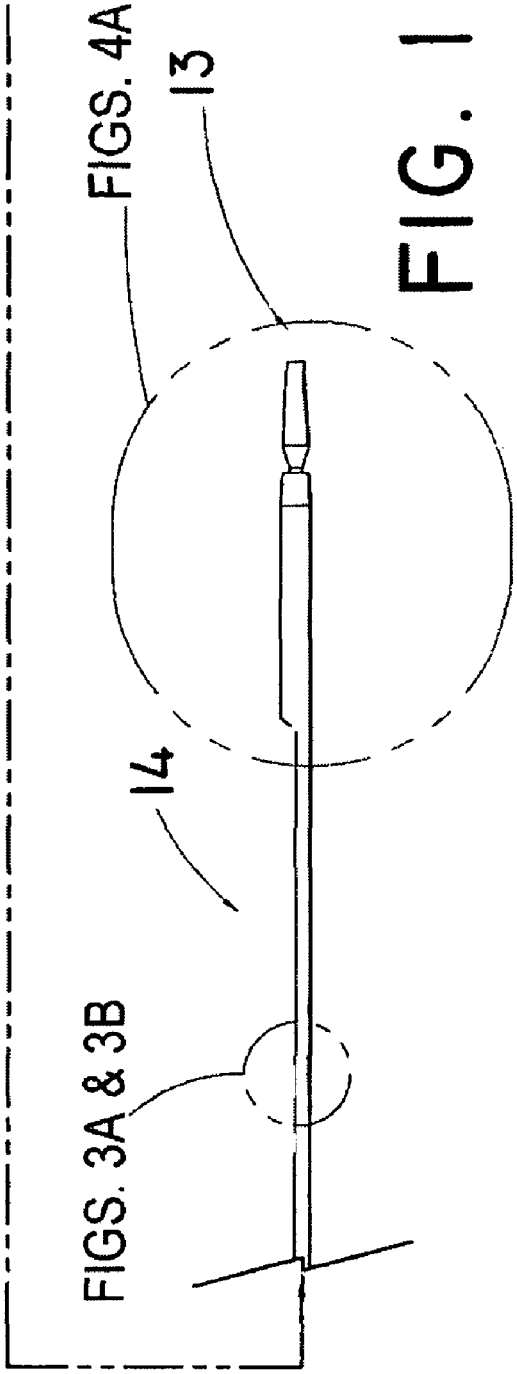
FIG. 1

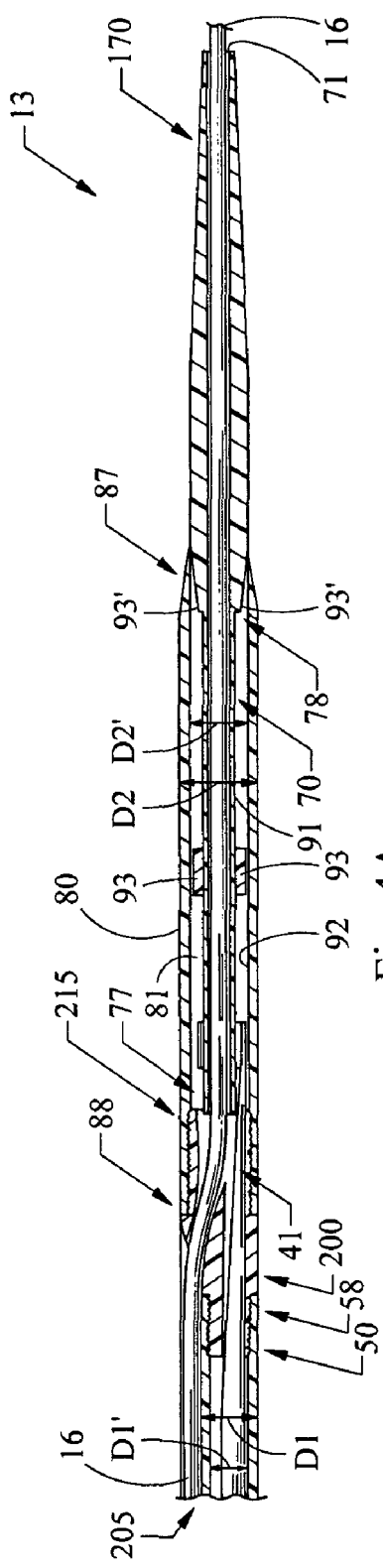
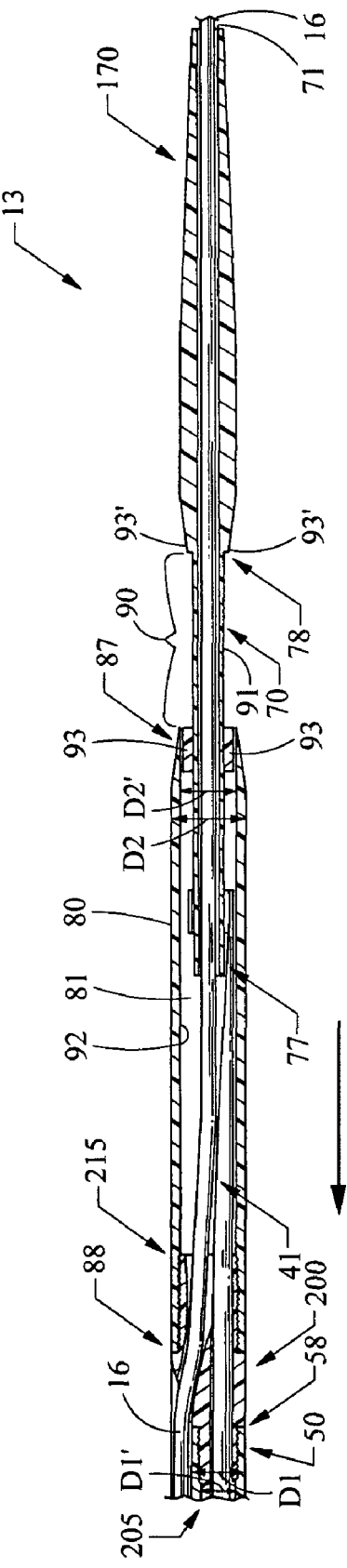
Fig. 4A
Fig. 4B

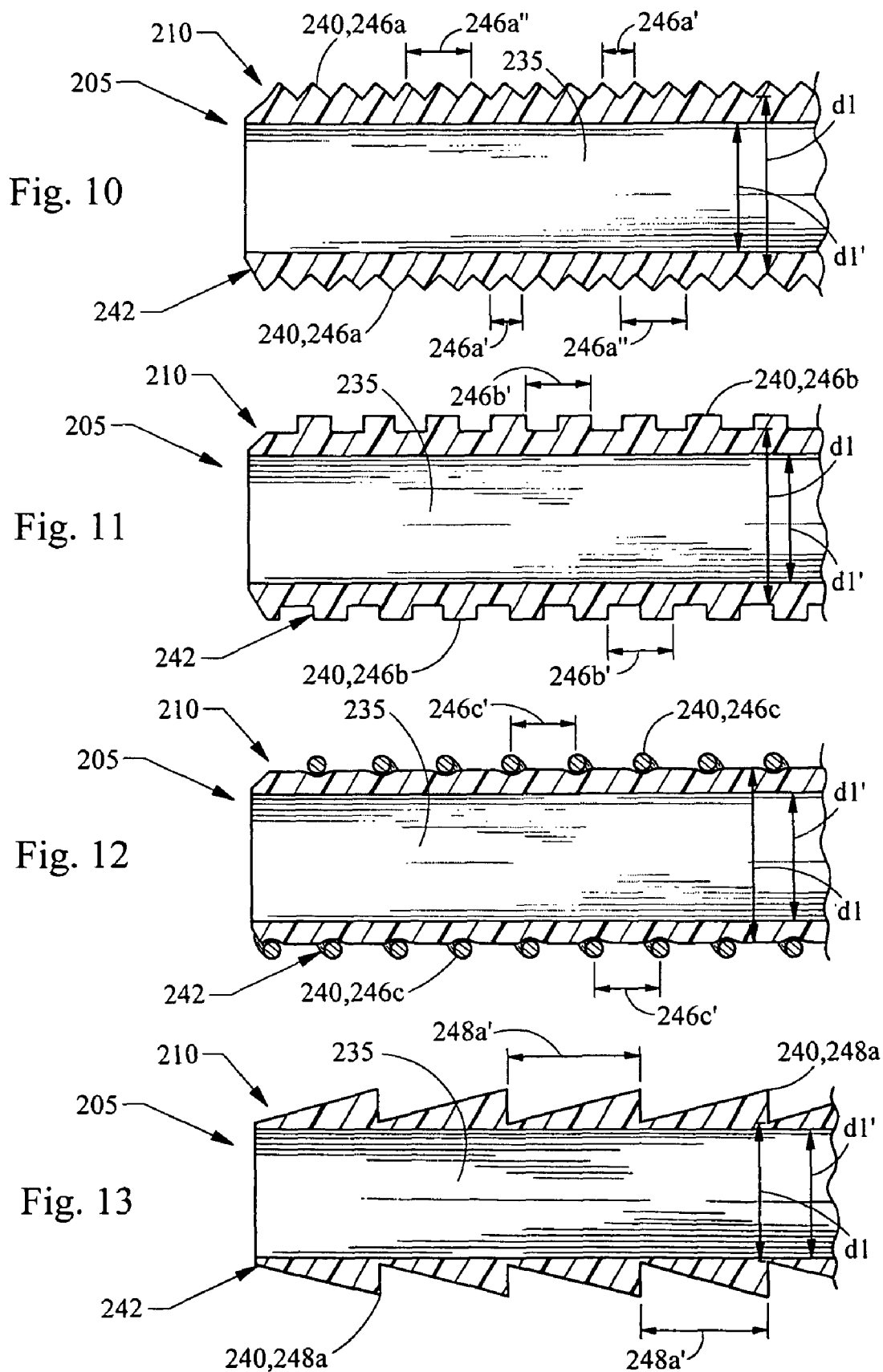

INSERT FOR COUPLING SHEATHS USED IN MEDICAL DEVICES

RELATED APPLICATIONS

The present patent document claims the benefit of the filing date under 35 U.S.C. §119(e) of Provisional U.S. Patent Application Ser. No. 60/673,199, which was filed on Apr. 20, 2005 and is hereby incorporated by reference.

TECHNICAL FIELD

This disclosure relates generally to the field of medical devices and more particularly to an insert for use with an intraluminal medical device delivery system.

BACKGROUND

Intraluminal medical delivery systems may be configured to deliver a self-expanding device, such as a stent, prosthetic valve device, or other implantable article, inside a patient's body. Medical delivery systems may also be configured for rapid insertion and removal. Such delivery systems have been described in the United States Provisional Patent Application filed on Apr. 20, 2005 and having an application Ser. No. 60/673,199 and client reference number PA-5598-PRV, the disclosure of which is incorporated in its entirety.

By way of background, stents are configured to be implanted into body vessels or passageways in order to reinforce, support, repair, or otherwise enhance the performance of the passageway. The term "passageway" is understood to be any vessel, lumen, channel, flow passage, duct, chamber, opening, bore, orifice, or cavity for the conveyance, regulation, flow, or movement of bodily fluids and/or gases. As an example, stents have been used in the passageways of the aorta, arteries, bile duct, blood vessels, bronchiole, capillaries, esophagus, fallopian tubes, heart, intestines, trachea, ureter, urethra, veins, and other locations (collectively, "vessel") in the body.

One type of stent is self-expanding. For a self-expanding stent, the stent is resiliently compressed into a collapsed first, smaller diameter, carried by the delivery system, and due to its construction and material properties, the stent expands to its second, larger diameter upon deployment. In its expanded configuration, the stent exhibits sufficient stiffness so that it will remain substantially expanded and exert a radially outward force in the vessel passageway on an interior surface of the vessel. One particularly useful self-expanding stent is the Z-stent, introduced by Cook Incorporated, due to its ease of manufacturing, high radial force, and self-expanding properties. Examples of the Z-stent are found in U.S. Pat. Nos. 4,580,568; 5,035,706; 5,282,824; 5,507,771; and 5,720,776, the disclosures of which are incorporated in their entirety.

A wire guide can be used to place a self-expanding stent delivery system into a vessel passageway percutaneously. The typical wire guide has proximal and distal ends. A physician inserts the distal end into the vessel passageway, advances, and maneuvers the wire guide until the distal end reaches its desired position within the vessel passageway.

Many delivery systems employ a tubular catheter, sheath, cannula, introducer, or other medical delivery device (individually and collectively, "catheter") having first and second ends and comprising a lumen for receiving the wire guide. Optionally, these delivery systems may fit a working channel within an endoscope or an external accessory channel device used with an endoscope.

Generally stated, these delivery systems may fall into one of two categories. The first category to be used, and consequently the first to be discussed below, is commonly referred to as an "over-the-wire" system. The other category of delivery system is sometimes referred to as a "rapid exchange" catheter.

In the "over-the-wire" catheter delivery system, a physician places the catheter over the wire guide, with the wire guide being received into a lumen that extends the entire length of the catheter. In this over-the-wire type of delivery system, the wire guide may be back-loaded or front-loaded into the catheter. In back-loading an over-the-wire catheter delivery system, the physician inserts a distal portion of the catheter over the proximal end of the wire guide. In front-loading an over-the-wire catheter delivery system, the physician inserts the distal end of the wire guide into the catheter's lumen at or near the catheter's proximal end. The back-loading technique is more common when the physician has already placed the wire guide into the patient. In either case of front-loading or back-loading an over-the-wire catheter delivery system, the proximal and distal portions of the catheter will generally envelop the length of the wire guide that lies between the catheter first and second ends. While the wire guide is held stationary, the physician may maneuver the catheter through the vessel passageway to a part of the target site at which the physician is performing or intends to perform a treatment, diagnostic, or other medical procedure.

Unlike the over-the-wire system, where the wire guide lies within the catheter lumen and extends substantially the entire length of the catheter, in a "rapid exchange" catheter delivery system, by contrast, the wire guide occupies a catheter lumen extending through only a distal segment of the catheter. The so-called rapid exchange system comprises a proximal end, an elongate flexible middle section delivery device, and a distal end that is generally tubular.

The distal end, in general, comprises an inner guide channel member sized to fit slidably within an outer guide channel member that is substantially axially slideable relative to the inner member. The outer guide channel member and inner guide channel member further have entry and exit ports defining channels configured to receive a wire guide. A port includes any structure that functions as a portal, port, passage, passageway, opening, hole, cutout, orifice, or aperture, while a guide channel is understood to be any passageway, lumen, channel, flow passage, duct, chamber, opening, bore, orifice, aperture, or cavity that facilitates the passage, conveyance, ventilation, flow, movement, blockage, evacuation, or regulation of fluids or gases or the passage of a diagnostic, monitoring, scope, other instrument, or more particularly a catheter or wire guide.

A wire guide may extend from the outer and inner member entry ports, through the outer and inner member guide channels, and exit the distal end at or near a breech position opening located at or near a transition region where the guide channels and exit ports are approximately aligned relatively coaxially to facilitate a smooth transition of the wire guide. Furthermore, the outer guide channel member has a slightly stepped profile, whereby the outer member comprises a first outer diameter and a second smaller outer diameter proximal to the first outer diameter and located at or near the transition region.

The distal end also has a self-expanding deployment device mounting region (e.g., a stent mounting region) positioned intermediate the inner guide channel member entry and exit ports for releasably securing a stent. At the stent mounting region, a stent is releasably positioned axially intermediate distal and proximal restraint markers and sandwiched transversely (i.e., compressed) between the outside surface of the inner guide channel member and the inside surface of an outer guide channel member.

Turning to the proximal end of the rapid exchange delivery system, the proximal end, in general, comprises a handle portion. The handle portion has a handle that the physician grips and a pusher stylet that passes through the handle. The pusher stylet is in communication with—directly or indirectly through intervening parts—the inner guide channel member at the distal end. Meanwhile, the handle is in communication with—directly or indirectly through intervening parts—the outer guide channel member at the distal end. Holding the pusher stylet relatively still while actuating the handle thereby keeps the stent mounting region at the inner guide channel member properly positioned at the desired deployment site. At the same time, proximally retracting the handle results in a corresponding proximal movement of the outer guide channel member relative to the inner guide channel member thereby exposing and, ultimately, deploying the self-expanding stent from the stent mounting region. At times, a physician may need to deploy a second self-expanding stent by withdrawing the system from the proximal end of the wire guide and then reloading the catheter onto the wire guide with an additional stent, or by replacing the delivery system with a catheter or different medical device.

The delivery system in the rapid exchange delivery system further comprises an elongate longitudinal flexible middle section delivery device extending intermediate the proximal end and the distal end. The middle section delivery device comprises an outer sheath and an inner compression member having first and second ends associated with the distal end and proximal end, respectively.

More particularly, the outer sheath distal end may be coterminous with or, if separate from, may be associated with (e.g., joined or connected directly or indirectly) the distal end outer guide channel member at or near the transition region, while the outer sheath proximal end is associated with the handle. The inner compression member first end is associated with the distal end inner guide channel member at or near the transition region, while the inner compression member second end is associated with the pusher stylet at the proximal end. Therefore, the outer guide channel member of the distal end may move axially (as described above) and independently relative to an approximately stationary inner guide channel member of the distal end and, thereby, deploy the stent.

Traditional ways of associating an outer sheath distal end and an outer guide channel member second end at a transition region include the use of glue, adhesives, and the like (collectively, "glue"). For example, a subassembly (or insert) may be adhered at a proximal end to the outer sheath and adhered at a distal end to the outer guide channel member. One must choose the right glue, however, to join dissimilar materials, and the glue must cure, thereby increasing the total processing (fixture) time in the application and assembly of the device.

Moreover, the glued portions of a subassembly may vary in strength and integrity depending on the congruity of the mating surfaces. In addition, if the subassembly material is not properly selected, the transition region may be too rigid, reducing the ability of the delivery system to navigate a tortuous path within the vessel passageway, or it may be too weak, and thus prone to kinking.

It would be desirable to provide an insert for joining sheaths in an intraluminal device delivery system that may be rapidly assembled, provide a secure coupling, and have a maneuvability and kink resistance which is similar to those of the sheaths.

BRIEF SUMMARY

Described herein is an insert for joining sheaths for use in a medical device which may be amenable to rapid assembly and may provide a secure coupling between the sheaths. The insert further may be designed to have a maneuverability and kink resistance matching the properties of the sheaths. This disclosure also provides a catheter including such an insert, and a method of assembling a catheter.

The insert includes a first operative coupling at a first end, and a second operative coupling at a second end. The first operative coupling is for engaging a first tube at its distal end, and the second operative coupling is for engaging a second tube at its proximal end. The insert also includes a first passageway extending through the insert from the second end to an exit port disposed between the first operative coupling and the second operative coupling.

The catheter includes a first tube, a second tube, and an insert including a first operative coupling at a first end and a second operative coupling at a second end. The first operative coupling is engaged to the first tube at its distal end, and the second operative coupling is engaged to the second tube at its proximal end. The insert also has a first passageway extending through the insert from the second end to an exit port disposed between the first operative coupling and the second operative coupling.

The method of assembling a catheter comprises the steps of providing a first tube, providing a second tube, and providing an insert. The insert includes a first end having a first operative coupling and a second end having a second operative coupling. The insert also includes a first passageway extending through the insert from the second end to an exit port disposed between the first operative coupling and the second operative coupling. The method also comprises engaging the first operative coupling with the first tube at its distal end, and engaging the second operative coupling with the second tube at its proximal end.

BRIEF DESCRIPTION OF THE DRAWINGS

FIG. 1 is a schematic view, broken away, of a medical device delivery system according to one embodiment;

FIGS. 4A and 4B are longitudinally sectioned views, broken away, of a distal end of medical device delivery system before (4A) and after (4B) retraction of the outer guide channel member, insert, and outer sheath, according to one embodiment;

FIG. 10 is a longitudinally sectioned view of an operative coupling including threads according to one embodiment;

FIG. 11 is a longitudinally sectioned view of an operative coupling including threads according to another embodiment;

FIG. 12 is a longitudinally sectioned view of an operative coupling including a threaded fitting according to another embodiment;

FIG. 13 is a longitudinally sectioned view of an operative coupling including barbs according to one embodiment;

DETAILED DESCRIPTION

Figure 2:
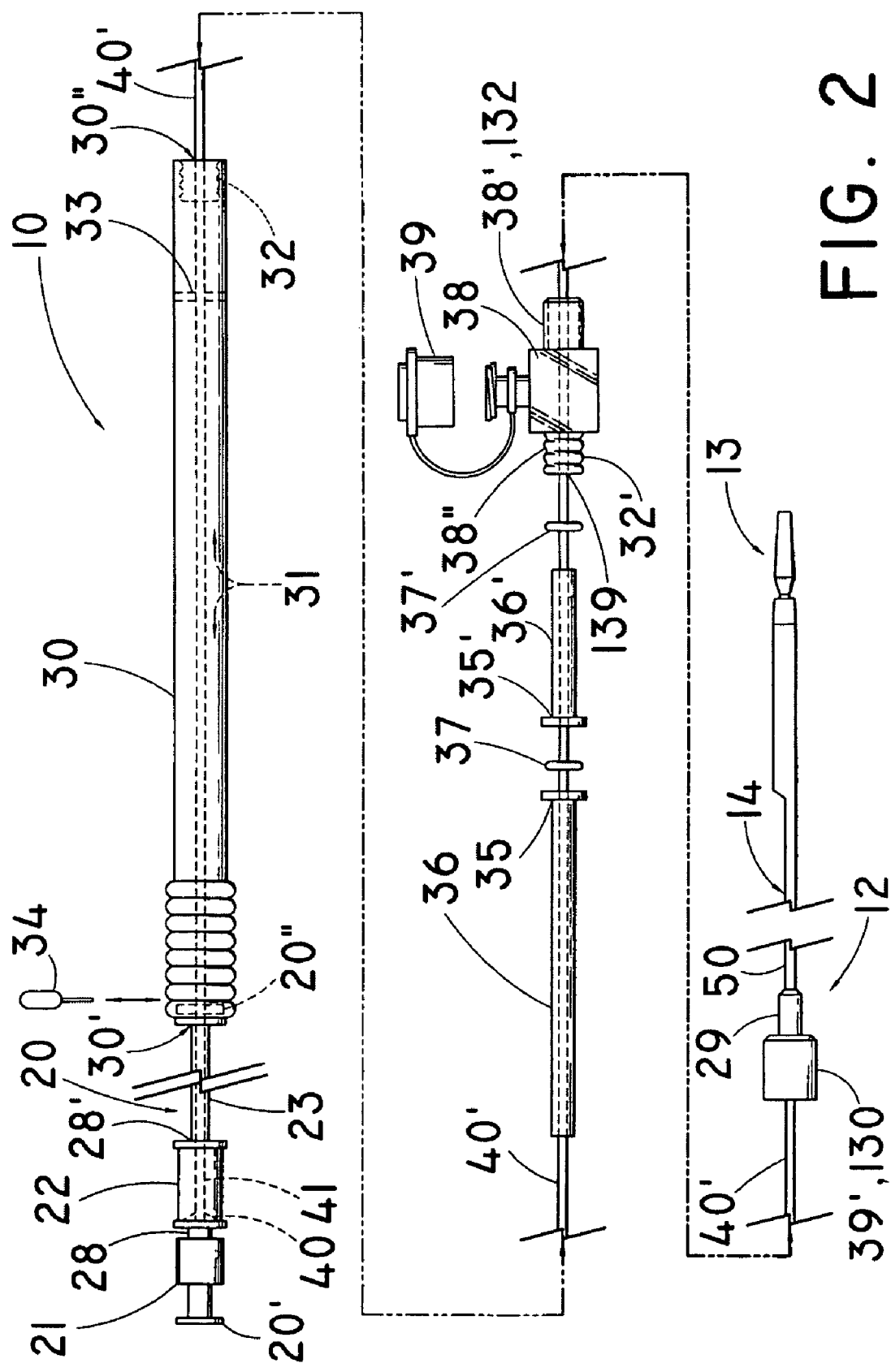
FIG. 2 is an exploded side view, broken away, of a proximal end of a medical device delivery system according to one embodiment.

The present disclosure relates to medical devices, and in particular to an insert for coupling sheaths used—by way of example only and not by way of limitation—for a rapid insertion delivery system configured to deliver expandable devices such as stents (e.g., self-expanding stents, balloon-expandable stents), prosthetic valve devices, and other implantable articles inside a patient's body. Otherwise stated, the present disclosure is applicable to a variety of medical devices that may require two sheaths to be coupled, and is not intended to be limited to an intraluminal medical device delivery system. For conciseness and ease of description of the embodiments described herein, the term "stent" and its variations shall refer individually and collectively (without limiting the invention) to all expandable devices, such as stents, prosthetic valve devices, and other implantable articles, that may be used inside a patient's body.

In FIG. 1, an illustrative embodiment of a stent delivery system 10 is provided. The delivery system 10 comprises a proximal end 12, a middle section delivery device 14, and a distal end 13.

Proximal End

In the embodiment shown in FIG. 1, the proximal portion 12 remains outside of the patient's body. The proximal portion 12 comprises a handle 30 and an optional pusher stylet 20.

FIG. 1 depicts a schematic representation of the handle 30 and the optional pusher stylet 20 shown more particularly in FIG. 2. In general, a handle 30 retracts an outer guide channel member (discussed below) of the distal portion 13 of the delivery system 10 to deploy a stent, as will be explained later. The handle 30 may comprise any mechanical, electromechanical, pneumatic, or hydraulic handle configured in communication with—directly or indirectly through intervening parts—the distal portion's outer guide channel member. Communication would include, by way of illustration and not by way of limitation, a handle 30 that uses or is otherwise associated with, directly or indirectly, an elongated mechanical wire, rod, shaft, cable, sheath, pneumatic tube, or hydraulic pistons, cylinders and/or flow paths configured for moving the outer guide channel member proximally in order to deploy a stent.

FIG. 2 provides a schematic view, broken away, of a delivery system 10 for rapid insertion of self-expanding stents, but could be used with other implantable prostheses described above. The delivery system 10 shown in FIG. 2 is one embodiment of the proximal portion 12, middle section delivery device 14, and distal portion 13 shown in a partially deploying position. The middle section delivery device 14 extends distally from the proximal portion 12, and a distal portion 13 extends to a position that is distal the middle section delivery device 14. More particularly, FIG. 2 shows an exploded view of the proximal portion 12 of the delivery system 10 according to one embodiment of the invention, with an emphasis on the handle 30 and the optional stylet 20. Features of one embodiment of a handle 30 and pusher stylet 20 are discussed below.

The handle 30 comprises any tubular structure having a distal aperture 30" and a proximal aperture 30', the apertures defining a chamber 31 therebetween. In general, the handle 30 is a component, instrument, mechanism, tool, device, apparatus, or machine configured for directly or indirectly retracting an outer guide channel member (discussed below) of the distal portion 13 of the device to expose and, ultimately, to deploy a stent self-expanding implantable prostheses such as stents, prosthetic valve devices, and other implantable articles (hereafter, "stent" or "stents") at a selected location inside a patient's body.

The handle 30 is axially slideable relative to an elongate (long) inner compression member 41 that comprises a proximal end 40 and a middle section 40'. As discussed more fully below, the inner compression member 41 helps to keep the stent from moving proximally with proximal movement of the handle 30, which handle movement causes the outer guide channel member to withdraw proximally over the stent in order to expose and thereby to deploy the stent. Thus, the inner compression member helps to "push" the stent or stent carrying inner guide channel member in order to counter the urge for the stent or stent carrying member to prolapse proximally with the withdrawing of the outer guide channel member. As will be understood, "pushing" on the inner compression member will keep the stent carrying inner guide channel member (and therefore the stent) from translating as a result of an outer sheath or outer guide channel member being pulled over the stent; thereby "pushing" holds the stent in place at the desired deployment site within the patient's body. In one embodiment, the handle 30 is a unidirectional handle that is axially slideable relative to the inner compression member 41 and/or the optional pusher stylet 20 in order to deploy a stent. In one embodiment, the inner compression member 41 is secured to a pusher stylet 20.

As shown in FIG. 2, one embodiment of a pusher stylet 20 comprises a proximal end 20', a distal end 20", and a cannula 23 intermediate the proximal and distal ends 20', 20", respectively, and a receptacle 22. The cannula 23, as should be understood, comprises any suitable hollow plastic or metal tube. As a hollow tube, the cannula 23 optionally allows the inner compression member 41 to pass proximally through the cannula 23 and to the proximal end 20' so that the inner compression member proximal end 40 (such as a flared proximal end 40) may secure to a plug 21 that fits within the receptacle 22, wherein FIG. 2 shows the proximal end 20', plug 21, and an optional securing material 28 are shown in an exploded view relative to the receptacle 22 into which they may be secured. Furthermore, the cannula 23 assists with keeping that portion of the inner compression member substantially straight.

The stylet 20 is optional, because in an alternative embodiment the physician may hold the inner compression member proximal end 40' directly in order to "push" (e.g., hold substantially stationary) the stent carrying inner guide channel member (and therefore the stent). This controls the stent carrying inner guide channel member and stent from translating as a result of an outer sheath or outer guide channel member being pulled over the stent, so that the stent remains at the desired deployment site within the patient's body. Alternatively, the stylet 20 is any stationary handle secured to the inner compression member 41 for achieving the "pushing" (e.g., hold substantially stationary) of the stent or stent carrying inner guide channel member while the outer sheath or outer guide channel member are moved proximally.

The stylet distal end 20" is housed within the handle chamber 31 and is flared or otherwise flanged sufficiently to be larger than the handle proximal aperture 30' so as not to pull out of the chamber 31. In one embodiment, the stylet distal end 20" is secured to the distal portion of the stylet cannula 23, while in another embodiment the stylet distal end 20" is formed integral with the distal portion of the stylet cannula 23. Consequently, the stylet distal end 20" functions as a proximal stop that prevents the stylet cannula 23 from backing all the way out the handle while being axially slideable within the handle chamber 31. Thus, the stylet 20 will not slide off the handle 30, if so desired. The stylet distal end 20" may also, in one embodiment, function as a distal stop against a restraint 33 formed in the handle chamber 31 intermediate the handle proximal and distal apertures 30', 30", respectively, where intermediate should be understood to be any position between, and not necessarily equidistant to, the handle apertures 30', 30". As a result of the stylet distal end 20", the handle 30 may slide axially the distance separating the handle restraint 33 and the stylet distal end 20", which has a maximum distance of when the stylet distal end 20" is abutting the handle proximal aperture 30'.

A threaded tapered plug 21 and threaded tapered receptacle 22 optionally secure the inner compression member proximal end 40. In one embodiment, the inner compression member proximal end 40 is flared. Securing material 28, such as glue, adhesives, resins, welding, soldering, brazing, chemical bonding materials or combinations thereof and the like (collectively and individually, "glue") may be used to keep the threaded tapered plug 21 from backing out of the threaded tapered receptacle 22. A portion of the cannula 23 and stylet distal end 20" are received within the handle chamber 31 distal to the handle proximal aperture 30' as previously explained.

By optionally placing the inner compression member proximal end 40 in mechanical communication with the plug 21 and receptacle 22, the gripping and "pushing" (e.g., hold substantially stationary) on the stylet 20 (e.g., the receptacle 22) thereby helps to keep the inner compression member 41 from moving away from the system distal portion 13 and, accordingly, counters the tendency for a stent or stent carrying member to move proximally during withdrawal of the outer guide channel member as will be explained below. Of course, the inner compression member may be secured elsewhere by the stylet 20, such as at or near the stylet distal end 20" or intermediate the stylet proximal and distal ends 20', 20", respectively, and the stylet distal end 20" may extend to a position at or near the distal end aperture 30" of the handle 30.

FIG. 2 shows a middle section 40' that extends distally from the proximal end 40 of the inner compression member 41. In one embodiment, the middle section 40' passes through the handle 30 (and may pass through the cannula 23 and/or bushings housed within the handle chamber 31 or other portions of the proximal portion 12). In one embodiment, the middle section 40' is elongate (at least 50.0 cm or longer as described below) and extends to a distance distally of the handle 30 and to a position at or near the medical system delivery device distal portion 13. It should be understood that, by describing the middle section 40' as passing through the handle 30, the middle section 40' does not necessarily need to pass proximally through the entire length of the handle 30, such as in an embodiment (by way of example and not by way of limitation) where the proximal end 40 of the inner compression member 41 is secured to a distal portion of the cannula 23 and/or the stylet distal end 20" extending within the handle chamber 31 to a position at or near the handle restraint 33.

In addition to holding a threaded tapered plug 21 and optionally the proximal end 40 of the inner compression member 41, the threaded tapered receptacle 22 may secure the proximal portion of the optional cannula 23. Glue 28' may be used at or near an interface of the cannula 23 and distal aperture of the threaded tapered receptacle 22. The glue 28' serves many functions, such as to keep dust from settling within the threaded tapered receptacle 22, to make the cannula 23 easier to clean, and to give aesthetics and a smooth feel to the device.

The handle 30 slidably receives the distal portion of the cannula 23 within the handle aperture 30' and handle chamber 31. As a result, the handle 30 is slidable relative to the stylet 20 (e.g., slidable relative to the threaded tapered plug 21, threaded tapered receptacle 22, and the cannula 23). In use, the physician grips the handle 30 in one hand and grips the stylet 20 (e.g., the receptacle 22) in the other hand. The physician holds the stylet 20 relatively stationary, which prevents the inner compression member and inner guide channel member and its stent carrying portion from moving proximally, and then withdraws the handle 30 proximally relative to the stationary stylet 20 and inner compression member 41. As a result, the physician is thereby retracting an outer guide channel member (discussed below) of the system distal portion 13 of the delivery system 10 to expose and, ultimately, deploy a stent locatable at the system distal portion 13 of the delivery system 10. The handle 30 is in communication with—directly or indirectly through intervening parts—the outer guide channel member at the system distal portion 13.

As shown in FIG. 2, some of those optional parts may include the following: a first bushing 36 having an optional first bushing flange 35; a second bushing 36' having an optional second bushing flange 35'; an intermediate seal 37 intermediate the first and second bushing flanges 35, 35', respectively; a second seal 37' intermediate the second bushing flange 35' and a check flow body 38; and a detachable cap 39, such a Luer cap by way of example but not by way of limitation. In one embodiment, one or both of the intermediate seal 37 and the second seal 37' is from a class such as an O-ring. In another embodiment, one or both of the intermediate seal 37 and the second seal 37' is a cylinder or disk with a center aperture, and may be made from material that comprises an O-ring. The bushings 36, 36' are hollow plastic or metal tubes that take up space within the handle 30 so that the inner compression member has less room to buckle. Fully assembled in one embodiment, the first bushing 36 is inserted within the cannula 23 and the first bushing flange 35 is distal to and abutting the handle restraint 33, which is sized to interfere with the bushing flange 35 to prevent the bushing flange 35 from moving proximal to the handle restraint 33. The second bushing flange 35' is distal to and optionally abutting the bushing flange 35 so to prevent it from moving proximal the first bushing flange 35, and the second bushing 36' is inserted within an opening 139 of the check flow body 38. The intermediate seal 37 and the second seal 37' help to prevent fluids that could be used with the device (discussed below) from entering the handle chamber 31, which directs fluids distally, which fluids may be conveyed through an outer sheath 50 of the middle section delivery device 14 and system distal portion 13. In one embodiment, the handle restraint 33 is from a class such as a counterbore wherein the restraint 33 comprises, by way of example only and not by way of limitation, a flat-bottomed cylindrical enlargement of the handle chamber 31 sized for receiving a first bushing flange 35, an intermediate seal 37, a second bushing flange 35', and/or a check flow body proximal mating end 38" intermediate the restraint 33 and the handle distal aperture 30".

The handle 30 and check flow body 38 operatively couple with the handle distal aperture 30" receiving a check flow body proximal mating end 38" and being secured together by any suitable means, including but not limited to a crimp, friction fit, press fit, wedge, threading engagement, glue, adhesives, resins, welding (laser, spot, etc.), soldering, brazing, adhesives, chemical bonding materials, or combinations thereof. In one embodiment, the handle 30 comprises a coupling member 32 and the check flow body proximal mating end 38" comprises a coupling member 32', the coupling members 32, 32' being complementary to hold the handle 30 and check flow body proximal mating end 38" together. In one embodiment, the coupling members 32, 32' may form complementary threads. If it is desired to achieve quicker assembly for manufacturing purposes, then the coupling members 32, 32' may be an array of circumferential ridges that form an interference fit when pressed together. If a one-time snap fit is desired, then the coupling members 32, 32' may be circumferential ridges in the form of barbs. In another embodiment, the handle 30 and check flow body proximal mating end 38" may be put together and taken apart for servicing, in which case the coupling members 32, 32' may be circumferential ridges in the form of knuckle threads (e.g., circumferential ridges forming complementary undulating waves). The operatively coupled handle 30 and check flow body proximal mating end 38" according to these embodiments may be fixed such that they do not rotate relative to each other, or may rotate while preventing undesired axial separation.

During use, the detachable cap 39 may be detached or opened and the device flushed with saline to remove air in order to help keep air out of the patient. The intermediate seal 37 and the second seal 37' ensure that any flushed fluid moves distally in the device and does not back up into the handle 30, such as between the handle restraint 33 and the first bushing 36, into the handle chamber 31, or out the handle proximal aperture 30'. The detachable cap 39 (such as a Luer cap) keeps saline from backing out of the check flow body 38, air from flowing into the check flow body 38, and blood from rushing out during periods of high blood pressure inside the patient.

The medical device delivery systems 10 may be used to deploy an implantable prosthesis that is a balloon expandable or self-expanding stent, prosthetic valve device, or other implantable articles provided on the distal portion of a delivery system. In operation, a physician inserts the distal portion and at least a portion of the middle section delivery device into a vessel passageway, and advances them through the vessel passageway to the desired location adjacent the target site within the vessel passageway of a patient. In a subsequent step, the physician moves the handle proximally, which withdraws the outer sheath and/or the outer guide channel member and releasably exposes the stent for deployment. In another step, the physician inflates the expandable member, such as a balloon, positioned under the stent inner surface to plastically deform the stent into a substantially permanent expanded condition. The physician may inflate the expandable member injecting fluid such as saline from a syringe into inner compression member 41, via pusher stylet 20, through a Luer fitting at the proximal end 20'. Therefore, the fluid is directed distally to the expandable member, filling the expandable member chamber and expanding the stent. The physician then deflates the balloon and removes the catheter or delivery device from the patient's body.

In one embodiment as shown in FIG. 2, the handle 30 further comprises a check flow body distal mating end 38' and a connector cap 39' (optionally detachable) secured to the check flow body distal mating end 38', and a strain relief 29. In one embodiment, the connector cap 39' is from a class of fasteners such as nuts, and in one embodiment is a flare nut. The connector cap 39' functions to hold (or assist in holding in combination with the check flow body distal mating end 38') a flared proximal portion of an outer sheath 50 and/or a flared strain relief 29 disposed about (and optionally extending proximally from) that held portion of the outer sheath 50. The strain relief member 29 provides a kink resistant point where the outer sheath 50 connects to the connector cap 39' and/or the check flow body distal mating end 38'.

The check flow body distal mating end 38' and connector cap 39' may be operatively coupled mechanically, chemically, and/or chemical-mechanically. In one embodiment, the connector cap 39' is crimped, friction fitted, press fitted, and/or wedged into engagement onto the check flow body distal mating end 38'. In another embodiment for example, the check flow body distal mating end 38' and connector cap 39' are operatively coupled by glue, adhesives, resins, welding (laser, spot, etc.), soldering, brazing, adhesives, chemical bonding materials, or combinations thereof.

Yet another embodiment of the connector cap 39' comprises a handle first connector 130 and the check flow body distal mating end 38' comprises a handle second connector 132. The handle first and second connectors 130, 132, respectively, function to operatively couple a strain relief member 29 operatively coupled to the proximal portion of the outer sheath 50. In one embodiment, the handle first connector 130 is from a class of fasteners such as nuts, and in one embodiment is a flare nut. Optionally, the distal portion of the second bushing 36' is sized (but for the second bushing flange 35') to be received within a check flow body proximal opening 139 in communication with the second connector 132.

By way of example only and not by way of limitation, the terms "operatively coupling," "operatively coupled," "coupling," "coupled," and variants thereof are not used lexicographically but instead are used to describe embodiments of the invention having a point, position, region, section, area, volume, or configuration at which two or more things are mechanically, chemically, and/or chemical-mechanically bonded, joined, adjoined, connected, associated, united, mated, interlocked, conjoined, fastened, held together, clamped, crimped, friction fit, pinched, press fit tight, nested, wedged, screwed together and/or otherwise associated by a joint, a junction, a juncture, a seam, a union, a socket, threads, a melt bond, glue, adhesives, resins, welding (laser, spot, etc.), soldering, brazing, adhesives, chemical bonding materials, implanted arrangement, or combinations thereof.

Thus, the check flow body 38 provides an optional three way connector. The check flow body proximal mating end 38" and handle coupling member 32 are operatively coupled. The side port is controlled by the detachable connector cap 39. The body distal mating end 38' is operatively coupled to a second connector cap 39', or optionally the handle second connector 132 is received within and operatively coupled to a handle second connector cap 130.

The foregoing description of a proximal end portion 12 of a medical device delivery system 10 according to one embodiment of the invention may be one assembly during shipping, or may include a two-part assembly or more. Otherwise stated, the stylet 20 and handle 30 may be sold already combined or may be combined after purchase by inserting the stylet cannula 23 into the handle at the hospital via the threaded tapered plug 21 and threaded tapered receptacle 22. An optional safety lock 34 helps to ensure against unintentional actuation by preventing distal movement of the stylet distal end 20″ by extending inwardly within the handle chamber 30 through a slot in the handle outer wall distal to the handle proximal aperture 30′. Consequently, the optional safety lock 34 thereby maintains the handle 30 in an undeployed position until the physician is ready to deploy an implantable prosthesis (e.g., a self-expanding, balloon expandable, or non-expanding stent; prosthetic valve devices, and other implantable articles) at a selected location inside a patient's body.

Middle Section Delivery Device

The middle section delivery device 14 is intermediate the proximal end 12 and the distal end 13 of the delivery system 10. The term "intermediate" is intended to mean between, though not necessarily equidistant to, the distal tip of the distal end 13 and the proximal tip of the proximal end 12. Furthermore, the middle section delivery device 14 may overlap or be partially inserted into a portion of the distal end 13 and/or the proximal end 12. In another embodiment, a portion of the middle section delivery device 14 (such as the sheath 50 explained below) and outer guide channel member 80 (discussed below) may be an elongate tubular catheter or Flexor® sheath of integral construction.

According to the invention, a middle section delivery device 14 is a flexible, elongate (long, at least about 50.0 centimeters ("cm")) tubular assembly. In one embodiment, the middle section delivery device 14 is from approximately 100.0 centimeters ("cm") to approximately 125.0 cm for use when placing a distal end 13 of the invention within a patient's body, although it may be sized longer or shorter as needed depending on the depth of the target site within the patient's body for delivering the stent. The term "tubular" in describing this embodiment includes any tube-like, cylindrical, elongated, shaft-like, rounded, oblong, or other elongated longitudinal shaft extending between the proximal end 12 and the distal end 13 and defining a longitudinal axis. As used herein and throughout to describe embodiments of the invention, the term "longitudinal axis" should be considered to be an approximate lengthwise axis, which may be straight or may at times even be curved because the middle section delivery device 14, for instance, is flexible and the distal end 13 also may be substantially or partially flexible.

Figure 3A:
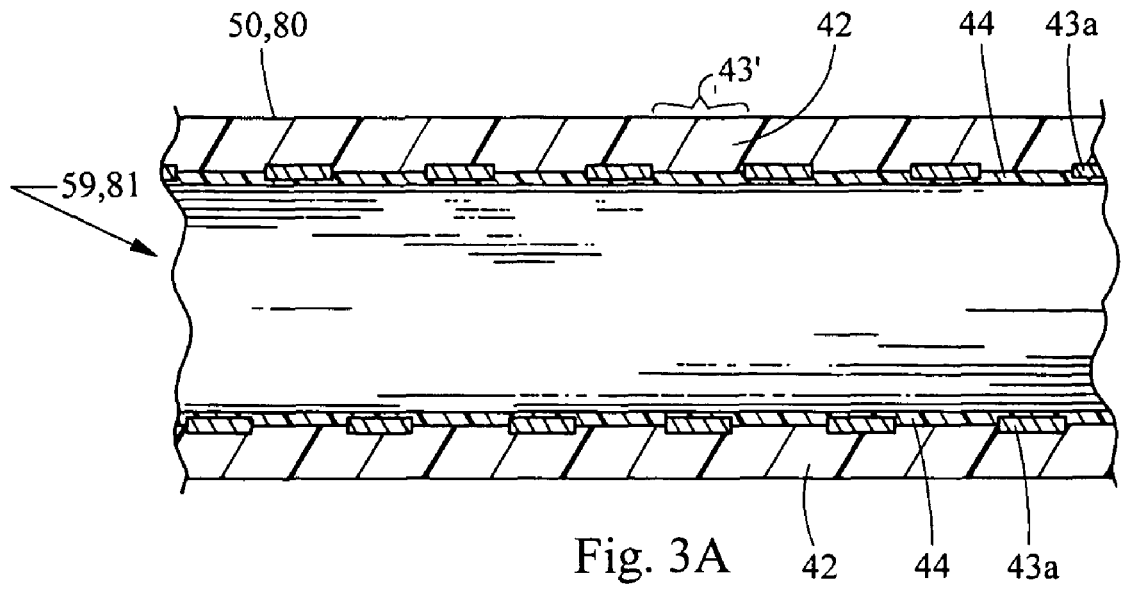
FIGS. 3A and 3B are longitudinally sectioned partial views of embodiments of an outer sheath and/or an outer guide channel member.
Figure 3B:
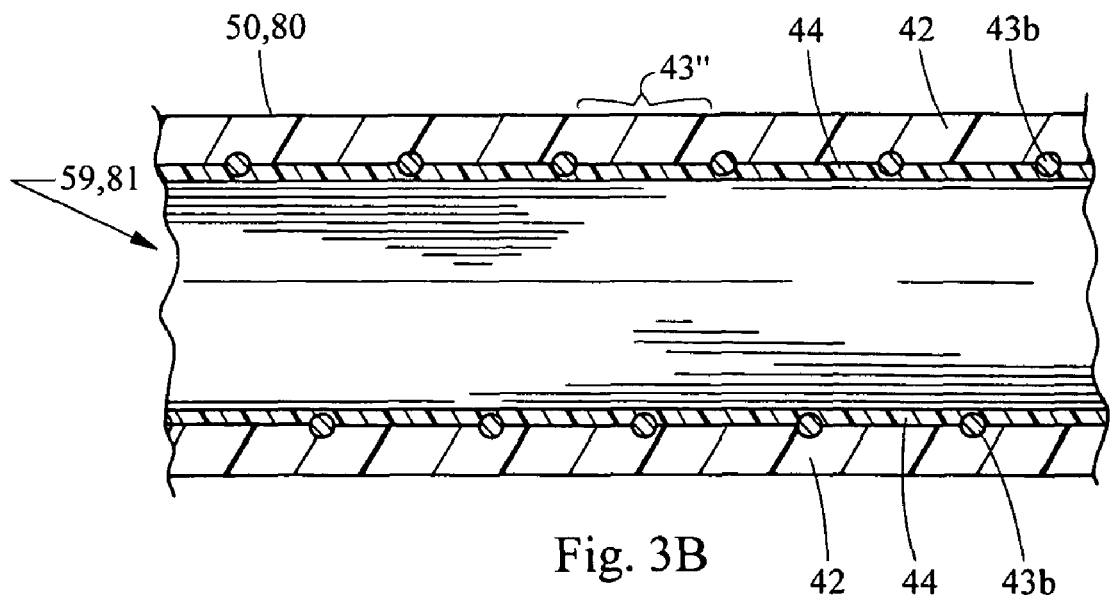

A middle section delivery device 14 comprises an outer sheath 50 containing a passageway 59. FIGS. 3A and 3B depict an enlarged, partially sectioned view of the middle section delivery device 14, with the delivery system's proximal and distal 12, 13 ends, respectively, of the device being removed for clarity. As discussed below, the middle section delivery device 14 may further comprise an elongate inner compression member 41 (not shown in FIGS. 3A and 3B; see FIGS. 4A and 4B).

In one embodiment, the wall of the outer sheath 50 includes three layers: an inner layer 44, a middle layer comprising a reinforcement structure 43, and an outer layer 42. The inner layer 44 may include a polymer, such as, for example polytetrafluoroethylene (PTFE, or Teflon). The reinforcement structure 43 of the middle layer may include a metallic material, such as stainless steel, and have spacings between constituents of the structure, as will be further described below. The outer layer may include a polymer, such as a nylon or polyether block amide (PEBA). The outer layer may be bonded to the inner layer through the spacings of the reinforcement structure. According to one embodiment, both the outer layer 42 and the inner layer 44 may include a lubricious material, such as polytetrafluoroethylene (PTFE), to present a slideable surface to allow for easier insertion and retraction of the delivery device 14 when deploying a stent, as will be explained later.

Preferably, the inner layer 44 of the outer sheath 50 may have sufficient radial rigidity to minimize bulging, kinking, and the like under an internal radial expansile force. In other words, the inner layer 44 may resist an inner object from protruding or becoming embedded into the inner layer 44, which is beneficial to the slideability of an outer sheath 50.

The reinforcement structure 43 may be compression fitted, wound, or otherwise disposed about the inner layer 44. The reinforcement structure 43 may be formed of any suitable material that will provide appropriate structural reinforcement, such as stainless steel, nickel-titanium alloys, or other metals, alloys, polymers, or composite materials that are either biocompatible or capable of being made biocompatible.

The reinforcement structure 43 may take the form of a coil, braid, mesh, or other structure that includes spacings between constituents. For example, the reinforcement structure 43 may be a coil that includes a plurality of turns with spacings 43′ between the turns, as shown, for example, in FIGS. 3A and 3B. FIG. 3A shows a flat ribbon shaped wire coil 43a as the reinforcement structure 43. However, coils of other cross-sectional shapes, such as round wire coil 43b, also may be used as the reinforcement structure 43, as shown in FIG. 3B. When flat wire stainless steel is used, the coil is optionally formed from wire that is about 0.003 inches thick by about 0.012 inches wide. In one embodiment, the turns of the coil are uniformly spaced 43′ apart by approximately 0.0118 inches. FIGS. 3A and 3B show embodiments that use coils 43a, 43b having uniformly spaced turns 43 and a constant pitch; however, this is not required and coils may be spaced apart by non-uniform distances or at varying distances. In one embodiment, the ends of the coil are positioned approximately 0.197 inches proximal to the distal end 13 and approximately 0.591 inches distal to the proximal end 12.

The outer sheath 50, the inner guide channel member 70, and outer guide channel member 80 for use with the middle section 14 and distal end 13 are available for purchase from Cook Incorporated, of Bloomington, Ind. under the trade name of "Flexor®." Examples of Flexor® sheath devices, materials, and methods of manufacturing may be found in U.S. Pat. Nos. 5,700,253 and 5,380,304, the contents of which are incorporated herein by reference. The Flexor® sheath may be particularly suited for the middle section 14 and/or the distal second end 13 due to its thin PTFE inner layer 44, thin flat wire coil reinforcement structure 43, and Nylon and/or PEBA outer layer 42. The PTFE inner layer 44 of the Flexor® sheath provides a slick, smooth surface that slides relatively easily when retracted to expose, release, and deploy the stent, for example. The Flexor® sheath may facilitate movement of the outer sheath 50 relative to the inner compression member 41 and also movement of the outer guide channel member 80 relative to the inner guide channel member 70 during deployment of the stent.

As an alternative to purchasing the outer sheath 50 or the outer guide channel member 80 for use with the middle section 14 and/or distal end 13 from Cook Incorporated, one may manufacture the outer sheath and outer guide channel member from various component parts. For instance, one may purchase a tubular inner layer 44 comprising a lubricious material comprising a fluorocarbon such as polytetrafluoroethylene (PTFE or Teflon) from Zeus, Inc. in Orangeburg, S.C., and dispose that inner layer 44 over a mandrel. Alternatively, a sheet of material comprising Teflon may be positioned on a mandrel and formed into a tubular body for the inner layer 44 by any suitable means known to one skilled in the art.

The tubular inner layer 44 (whether formed from a sheet on a mandrel or purchased as a tube and slid onto a mandrel) may be slightly longer than the desired length described above for the outer sheath 50 and/or outer guide channel member 80, and slightly longer than the mandrel. In one embodiment, the tubular inner layer 44 may extend about 5.0 cm from each mandrel end. As explained below, the "loose" ends of the tubular inner layer 44 may assist during manufacturing of the device.

The mandrel-tubular inner layer 44 assembly may be prepared for a middle layer comprising a reinforcement structure 43, such as, for example, a stainless steel circumferential spiral coil as described above and available for purchase from Cook Incorporated or Sabin Corporation of Bloomington, Ind. As purchased, the coil comes in a long, pre-coiled configuration and may be cut by hand or machine to the desired length either before or after winding the coil about the inner layer 44 to the desired length. As an alternative, one may manufacture the reinforcement structure 43 from raw material available from Fort Wayne Medical in Fort Wayne, Ind., for example, and process it into the desired configuration, such as a spiral coil, braid, mesh or other arrangement.

The operator may apply the reinforcement structure 43 about the mandrel-tubular inner layer 44 assembly by hand or machine. If applied by hand, then, in the case of spiral coil configuration, an end of the wire may be started onto the tubular inner layer 44 by any suitable means, such as, for example, by hooking and winding (e.g., wrapping) about the tubular inner layer 44 in a pigtailed manner. The initial position may be at a desired distance (e.g., 5.0 cm) from a first end of the tubular inner layer 44. The terminating position upon cutting the wire may be at a desired distance (e.g., 5.0 cm) from a second end of the tubular inner layer 44. If applied by machine, the wire may be threaded through an arm on a machine and started onto the tubular inner layer 44 at the initial position as described above while chucks, for instance, hold the opposing ends of the mandrel-tubular inner layer 44 assembly. As the chucks rotate, the inner layer 44 rotates, and the arm moves axially down the length of the inner layer 44, thereby applying the wire in a spiral configuration about the inner layer 44. The machine arm moves to a terminating position where the machine or operator cuts the wire before or after hooking the wire 43 onto the inner layer 44.

An operator then may apply an outer layer 42 about the reinforcement structure-inner layer-mandrel assembly. The outer layer 42 may comprise a polymer such as a polyether block amide, nylon, and/or a nylon natural tubing (individually and collectively, "PEBA" and/or "nylon"). The outer layer 42 preferably has a tubular configuration disposed about (i.e., enveloping, surrounding, wrapping around, covering, overlaying, superposed over, encasing, ensheathing, and the like) a length of the reinforcement structure-inner layer-mandrel assembly.

Heat shrink tubing, available from many suppliers, including Zeus, Inc. in Orangeburg, S.C., may be disposed about the outer layer-reinforcement structure-inner layer-mandrel assembly. Heating the assembly causes the outer layer 42 to soften, flow and/or melt. The inner surface of the outer layer 42 may seep through spaces 43' between constituents of the reinforcement structure 43 and bond to the outer surface of the inner layer 42. The outer layer 42 may also bond to the reinforcement structure 43. Up on cooling, a solid-state bond may result such that the assembly comprises the three layers discussed above. The operator may then remove the shrink wrap by, for example, cutting, and withdraw the mandrel. The operator may cut the Flexor® sheath to a desired length for an outer sheath 50 and/or outer guide channel member 80.

The temperature, total rise time, and dwell time for the heat shrink-outer layer-reinforcement structure-inner layer-mandrel assembly may vary depending on many factors including, for instance, the materials used and the diameter of the desired Flexor® sheath. For example, the baking parameters for a 2.5 French Flexor® sheath may be approximately 380 degrees Fahrenheit for about five minutes, while the baking parameters for a 4 French Flexor® sheath may be approximately 380 degrees Fahrenheit for about six minutes.

As an alternative to a Flexor® sheath, the outer sheath 50 may comprise a construction of multifilar material. Such multifilar material or tubing may be obtained, for example, from Asahi Intec USA, Inc. (Newport Beach, Calif.). Materials and methods of manufacturing a suitable multifilar tubing are described in Published United States Patent Application 2004/0116833 (Koto et al.), the contents of which are incorporated herein by reference. Use of multifilar tubing in a vascular catheter device, for instance, is described in U.S. Pat. No. 6,589,227 (Sonderskov Klint, et al.; Assigned to Cook Incorporated of Bloomington, Ind. and William Cook Europe of Bjaeverskov, Denmark), which is also incorporated by reference.

In addition to the outer sheath 50, the middle section delivery device 14 further comprises an inner compression member 41 (see FIGS. 4A and 4B). The delivery device 14 may be constructed to have any diameter and length required to fulfill its intended purpose. Thus, the outer sheath 50 and the inner compression member 41 may also have any suitable diameter (or width) and length.

The outer sheath 50, for instance, may be available in a variety of lengths, outer diameters, and inner diameters. In one embodiment, the outer sheath 50 may have a substantially uniform outer diameter in the range of from approximately 2 French to approximately 7 French, with a preferred embodiment of from approximately 4 French to approximately 5 French in diameter. Otherwise stated, the outer sheath 50 may range from about 0.010 inches to about 0.090 inches in diameter, and in one embodiment the diameter is approximately 0.050 inches.

According to one embodiment, the inner diameter of the outer sheath 50 ranges from about 0.032 inches to about 0.040 inches, and in a preferred embodiment the inner diameter is approximately 0.032 inches. The outer diameter and inner diameter of the outer sheath 50 may be more or less than these examples, however, depending on the intended vessel passageway for the device.

Likewise, the overall length may vary. In one embodiment, the outer sheath 50 may have a length from about 50.0 cm (or about 19.685 inches) to about 125.0 cm (or about 49.213 inches), and more particularly from about 70.0 cm (or about 27.559 inches) to about 105.0 cm (or about 41.339 inches), and in a preferred embodiment the length is approximately 100.0 cm (or about 39.370 inches).

The inner compression member 41 comprises an elongated pusher bar, stiffening member, or stiff polymer that helps to maintain the stent platform (the inner guide channel member 70) substantially stationary relative to the proximal retraction of the distal outer guide channel member 80 during deployment of the stent. In other words, the inner compression member helps to prevent or minimize prolapse, recoil kinking, or unwanted movement of the inner guide channel member 70.

The overall length of the inner compression member 41 may vary, as desired. In one embodiment, the inner compression member 41 has a length of from about 50.0 cm to about 175.0 cm, and more particularly between about 75.0 cm and 150.0 cm. In another embodiment the length is in the range of from approximately 125.0 cm to about 140.0 cm. A portion of the inner compression member 41 proximal end 40 may be contained within the handle 30 and the stylet 20, as explained above.

Likewise, the diameter or width of the inner compression member 41 may vary. In one embodiment, the inner compression member 41 has a diameter or width ranging from about 0.010 inches to about 0.020 inches, by way of example only and not by way of limitation. In a preferred embodiment, the inner compression member 41 has a diameter or width that is approximately 0.016 inches. The diameter or width may be more or less than these illustrative ranges. For example, a deeper target site within a patient may require a thicker (i.e., larger in diameter or wider) inner compression member 41 for greater pushability. Alternatively, a deeper target site may benefit from an inner compression member 41 of the same dimensions, but comprising a different material. In other words, a thinner inner compression member 41 made of stiffer material may have the same pushability of a thicker inner compression member 41. The inner compression member 41 may have a curved transverse cross-section, such as, for example, a circular or elliptical cross-section, or it may have a polygonal cross-section, such as, for example, a rectangular or square cross-section. Alternatively, the transverse cross-section of the inner compression may include both curved and straight portions. According to one embodiment, the inner compression member 41 may have a nonuniform diameter or width along its length. It may, for example, taper toward the distal end.

According to another embodiment, the inner compression member 41 may comprise a passageway (e.g., hollow, having a lumen) that facilitates the conveyance, ventilation, flow, inflation, movement, blockage, evacuation, or regulation of medication and/or fluids or accommodates the insertion of a diagnostic, monitoring, scope, or other instrument. Such a tubular inner compression member 41 may have a uniform inside diameter ranging from about 0.0527 to about 0.132 inches. The wall thickness of the tubular inner compression member 41 may be approximately 0.0015 inch. These dimensions are illustrative only, and the inner diameter and wall thickness may be constructed to be of any size necessary to accomplish the purposes for which the device is to be employed (i.e., limited by the vessel passageway or working channel in which the device is to be used).

Also, the inner compression member 41 may have an outer surface comprising a lubricious PTFE material and/or an inner layer 44 of the outer sheath 50 may comprise a lubricious PTFE material, in order to allow easy retraction of the outer sheath 50 with respect to the inner compression member 41.

Optionally, the inner compression member 41 and outer sheath 50 may have approximately the same length. The axial length of the reinforcement structure 43 generally may be less than the length of the inner compression member and outer sheath. According one embodiment, the inner compression member 41 stops short of extending all the way to the distal tip of the device, and may terminate at a distal end located from about 10 cm to about 40 cm away from the distal tip. In one embodiment, the distal end of the inner compression member 41 is disposed from about 20 cm to about 25 cm away from the distal tip of the outer sheath. The distal end of the inner compression member 41 may be lap jointed (e.g., by melt bonding) to a proximal portion of an inner guide channel member 70.

Distal End

Now turning to an embodiment of a distal end 13 of a device, the distal end is a relatively tubular body. Given the configuration of vessels, vessel passageways, a working channel of an endoscope, or an external accessory channel device used with an endoscope to be navigated, a mostly tubular distal end with a distal tapered, rounded, chamfered, or arrowhead shape may be better tolerated by the patient. Further, in certain embodiments, the distal portion of the distal end 13 may be soft, rounded, and flexible so as to provide further protection for and care to the patient.

FIGS. 4A and 4B illustrate an embodiment of the distal end 13 of a delivery system for the rapid insertion of self-expanding stents comprising an inner guide channel member 70, an outer guide channel member 80 axially slideable relative to the inner member 70, and a self-expanding deployment device mounting region 90 (e.g., a stent mounting region). As used in connection with describing embodiments of the inner and outer members 70, 80, the term "guide channel" is understood to be any passageway, lumen, channel, flow passage, duct, chamber, opening, bore, orifice, aperture, or cavity that facilitates the passage, conveyance, ventilation, flow, movement, blockage, evacuation, or regulation of fluids or gases or the passage of a diagnostic, monitoring, scope, other instrument, and more particularly a catheter, another component of the distal end (e.g., an inner member 70 relative to the outer member channel 81), or a wire guide 16 (not shown).

The distal end 13 may be made of any suitable material (natural, synthetic, plastic, rubber, metal, or combination thereof) that is rigid, strong, and resilient, although it should be understood that the material may also be pliable, elastic, and flexible. By way of illustration only, and not by way of limitation, the following are exemplary materials suitable for the distal end: nickel-titanium alloy (such as Nitinol), polyether ether-ketone ("PEEK"), polyimide, polyurethane, cellulose acetate, cellulose nitrate, silicone, polyethylene terephthalate ("PET"), polyamide, polyester, polyorthoester, polyanhydride, polyether sulfone, polycarbonate, polypropylene, high molecular weight polyethylene, polytetrafluoroethylene, or mixtures or copolymers thereof, polylactic acid, polyglycolic acid or copolymers thereof, polycaprolactone, polyhydroxyalkanoate, polyhydroxy-butyrate valerate, polyhydroxy-butyrate valerate, or another polymer or suitable material. Where it will not contact the patient (e.g., it is contained within a sheath, working channel of an endoscope, or an external accessory channel device used with an endoscope), the middle section 14 and distal end 13 do not need to be biocompatible. In contrast, where there is the possibility of patient contact, the material may need to be biocompatible or capable of being made biocompatible, such as by coating, chemical treatment, or the like.

The inner and outer guide channel members 70, 80, respectively, may be made of any suitable material described above for use with the distal end 13. In one embodiment, the inner member 70 and the outer member 80 comprise PEEK, which has the advantage of softening under heat before burning or degrading. PEEK tubing may be purchased from many suppliers, such as Zeus, Inc. in Orangeburg, S.C.

Beginning with the inner member 70, a description will follow relating to an embodiment of a distal end 13 of a rapid insertion delivery system 10 for the deployment of self-expanding stents. The inner member 70 is generally tubular and comprises a first end 78 and a second end 77. In one embodiment, the inner member 70 is a cannula (or catheter) including a guide channel 71. Optionally, the inner member 70 is configured to be slidably nested, fitted, secured, or otherwise positioned within the outer member 80 such that at least one of the inner member first or second ends 78, 77, respectively, is axially intermediate an outer member first end 88 and an outer member second end 87.

The inner member 70 further comprises an outer self-expanding deployment device mounting region 90 (e.g., an outer stent mounting region). The length of the inner member 70 may vary generally from about 10.0 to about 40.0 cm. In one alternative embodiment, the length of the inner member 70 is approximately 15.0 to approximately 25.0 cm. In another embodiment, the length of the inner member 70 is approximately 20.0 cm. Also, the length of the inner member 70 may depend on the intended stent, and in another embodiment the length of the inner member 70 is approximately 15.0 cm for an 8.0 cm stent. In one embodiment, the inner member 70 has an internal diameter that measures approximately 0.0205 inches, while the inner member proximal second end 77 has an outer diameter measuring approximately 0.0430 inches.

FIGS. 4A and 4B further show an atraumatic tip 170 at the inner member first end 78. Extending distally from the inner member first end 78, the atraumatic tip 170 has a tapered, rounded, chamfered, or arrowhead shape to be better tolerated by the patient. The atraumatic tip 170 includes the wire guide channel 71. The proximal end of the atraumatic tip 170 may be configured to have a beveled design that forms a stent distal restraint 93' as explained below. The atraumatic tip 170 may be an integral part of the inner guide channel member 70, or it may be formed as a separate unit and attached to the inner member 70 using methods known in the art.

The outer guide channel member 80 also is generally tubular and comprises a first end 88 and a second end 87 with a guide channel 81 disposed between the first end 88 and the second end 87.

The Flexor® sheath, manufactured and sold by Cook Incorporated of Bloomington, Ind., may be used for either the middle section 14 or the distal end 13, or both. Then, the separable middle section 14 and distal end 13 may be attached, adjoined, joined, or combined as taught in the United States Provisional Patent Application filed on Apr. 20, 2005 and having an application Ser. No. 60/673,199 and client reference number PA-5598-PRV, the disclosure of which is incorporated in its entirety, and as further described below.

The Flexor® sheath has a PTFE inner lining 44 that may provide a slick, smooth surface for sliding the outer sheath 50 and/or the outer guide channel member 80 proximally. With regard to the distal end 13, the outer member 80 slides relative to the inner member 70, and the outer member inner wall 92 would be the inner layer 44 described above, thereby resulting in minimal friction to a stent 17 on the stent platform 91. The slidable inner wall 92 of the Flexor® sheath exhibits a second benefit of minimizing damage or misalignment to the stent. Indeed, because self-expanding stents continuously exert an expanding force against the inner wall 92 of the outer guide channel member 80, any substantial friction or drag between the stent and the inner wall 92 of the outer member 80 as the outer member 80 withdraws may damage the stent or cause the stent to be deployed slightly off of the target site.

The thin flat wire coil 43a (not shown in FIGS. 4A and 4B) of the Flexor® sheath may provide the outer guide channel member 80 with the necessary radial strength to constrain the stent over long periods of storage time. In contrast, where the inner wall 92 of an outer member 80 does not comprise the Flexor® sheath inner layer 44, the stent over time may tend to become embedded in the inner wall 92 and, as a result, interfere with retraction of the outer member 80 at the time of deployment. An outer member 80 that comprises a Flexor® sheath has, in addition to the inner layer 44 and the reinforcing coil 43, an outer layer 42. The Flexor® sheath outer layer 42 comprises nylon and/or PEBA, which may provide the stiffness and pushability needed for retraction and control of the outer member 80, thus facilitating proper deployment of the constrained self-expanding stent.

As shown in FIGS. 4A and 4B, the distal end 13 also comprises a self-expanding deployment device mounting region 90. This mounting region 90 may be used for stents, prosthetic valve devices, and other self-expanding devices and implantable articles inside a patient's body (referred to individually and collectively as "stents" without limiting the invention) and may be referred to as a stent mounting region. This stent mounting region 90 comprises a stent platform 91 on an outside surface of the inner guide channel member 70 located at or near the inner member second end 78. The platform 91 is "at or near" the inner member second end 78. The phrase "at or near" as used herein includes a location that is at, within, or a short distance such as about 0.1 cm to about 15.0 cm, although other ranges may apply, for instance from about 0.5 cm to about 10.0 cm.

The platform 91 may be any stent mounting surface, including but not limited to the outside surface of the inner member 70, a recess, or an indentation located at or near the first end 78 of the inner member 70. In a non-deployed state, a self-expanding stent for example (not shown) is compressed against the stent platform 91 and disposed about the outside surface of the inner member 70.

The stent mounting region 90 controls the lateral movement (e.g., transverse expansion away from the inner member longitudinal axis) to avoid premature deployment of the stent. In order to control the lateral movement of the stent, the platform 91 on the inner surface of the stent and the inner wall 92 of the outer member 80 sandwich the stent therebetween (e.g., help to keep the stent in a compressed state). Because the stent is bound from above by the inner wall 92 of the outer member 80 and bound from below by the platform 91 of the inner member 70, the stent mounting region 90 maintains the stent in a substantially compressed state and controls premature deployment of the stent.

In addition to controlling a stent's lateral movement, the stent mounting region 90 restrains the axial or longitudinal movement of a stent to control the stent movement away from the target site. A proximal restraint 93 controls proximal axial movement of the stent. In one embodiment, the proximal restraint 93 is sized to be large enough to make sufficient contact with the loaded proximal end of the stent without making frictional contact with the inner wall 92 of the outer member 80. In addition to helping to stop the stent's proximal movement in the non-deployed state, this restraint 93 assists with "pushing" the stent out of the distal end 13 by helping to prevent the stent from migrating proximally when the outer member 80 retracts proximally relative to a stationary inner member 70 to deploy the stent. Optionally, the restraint 93 may be radiopaque so as to aid in stent positioning within the vessel passageway at or near the target site within a patient. In one embodiment, an optional distal restraint 93' is large enough to make sufficient contact with the loaded distal end of the stent to control distal movement of the stent. Similarly, in another embodiment the proximal end of an atraumatic tip 170 controls the stent's distal movement. Optionally, the distal restraint 93' and/or atraumatic tip 170 may comprise radiopaque materials so as to aid in stent positioning within the vessel passageway at or near the target site within a patient.

Insert for Coupling Sheaths

FIGS. 4A and 4B show an insert 200 operatively coupling the outer guide channel member 80 and the outer sheath 50 of the delivery system 10. Coupled together, the outer guide channel member 80 and the outer sheath 50 may be moved independently of the inner guide channel member 70, which may carry a self-expandable stent (not shown) for deployment in a vessel. By moving the handle 30 in an axial direction, a physician may retract the outer sheath 50 and the outer guide channel member 80 coupled to it via the insert 200, thereby allowing the undeployed stent to expand and contact a vessel wall. Retraction of the outer sheath 50, insert 200, and outer guide channel member 80 relative to the inner guide channel member 70 is illustrated in FIGS. 4A and 4B.

As used herein, the terms "operative coupling," "operatively coupling," "operatively coupled," "coupling," "coupled," and variants thereof are used to describe configurations or components enabling two or more things to be engaged, attached, joined, adjoined, conjoined, connected, associated, united, linked, mated, interlocked, fastened, secured, bound, bonded, press fit, friction fit, wedged together, screwed together, clamped together, crimped together, and/or held together.

Figure 5:
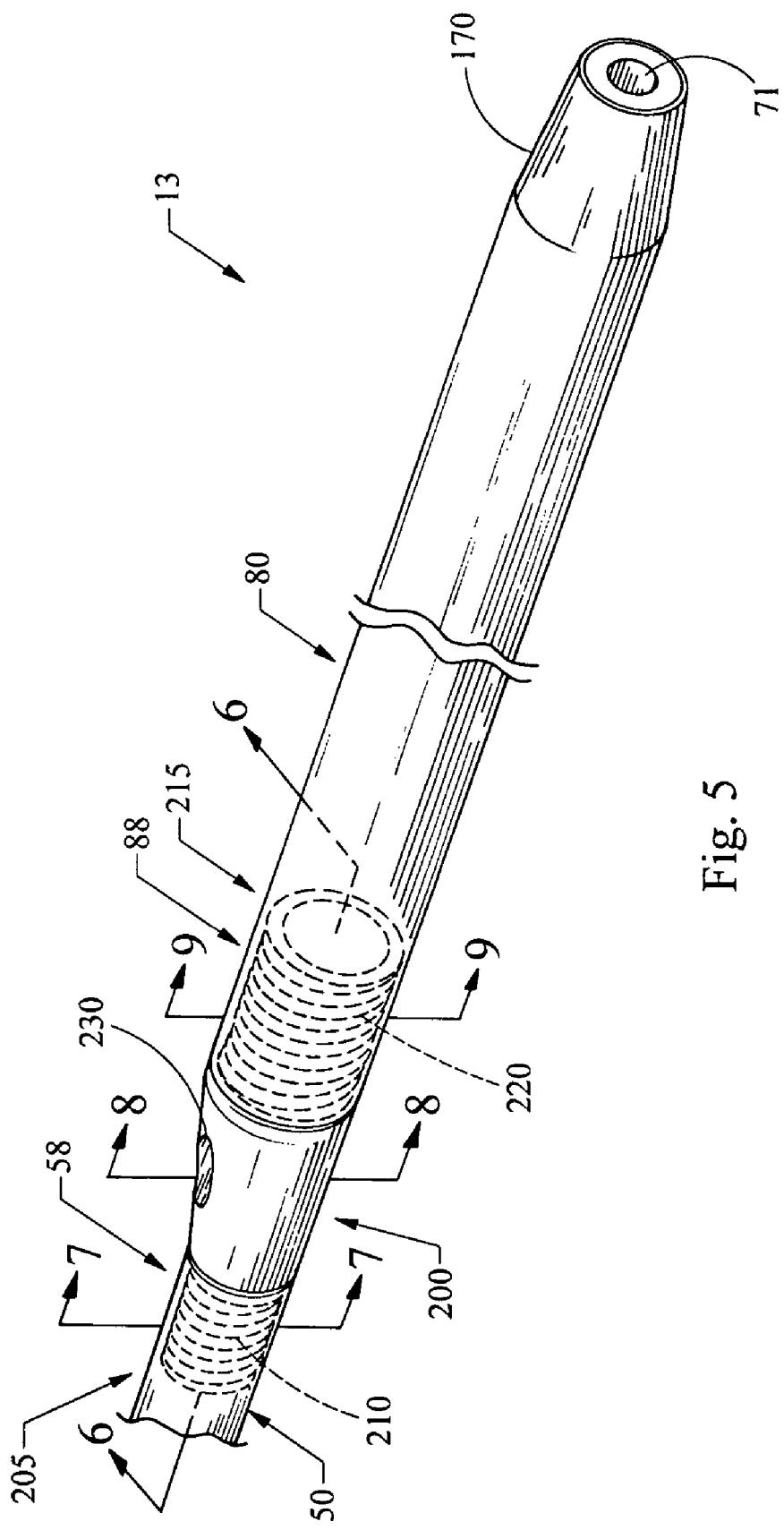
FIG. 5 is a perspective view of the insert coupled with the outer sheath and outer guide channel member, according to one embodiment.
Figure 6:
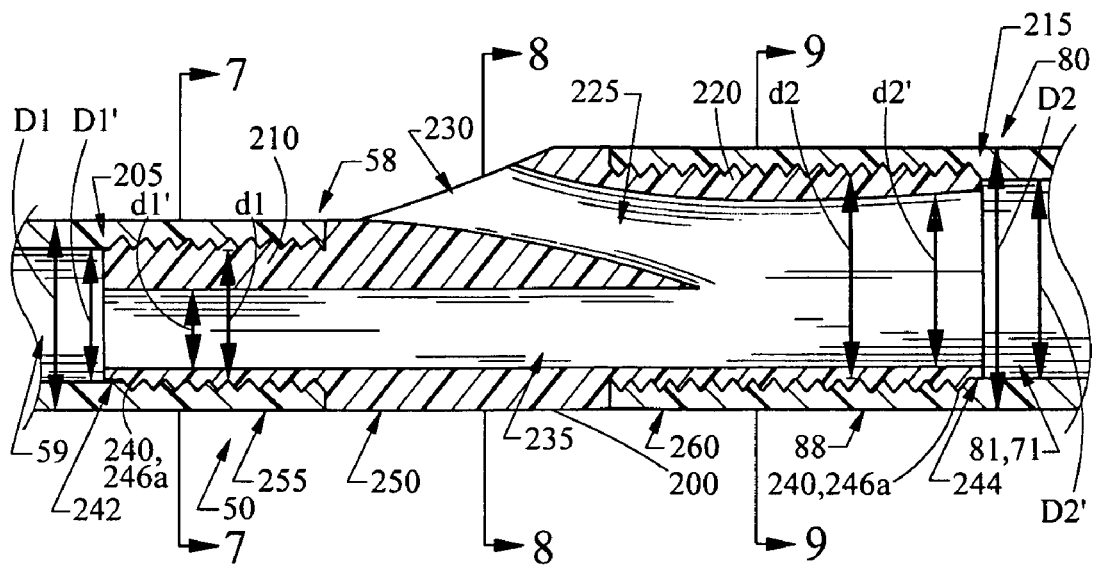
FIG. 6 is a longitudinal sectioned view of the insert, according to one embodiment, taken along section 6-6 in FIG. 5.
Figure 7:
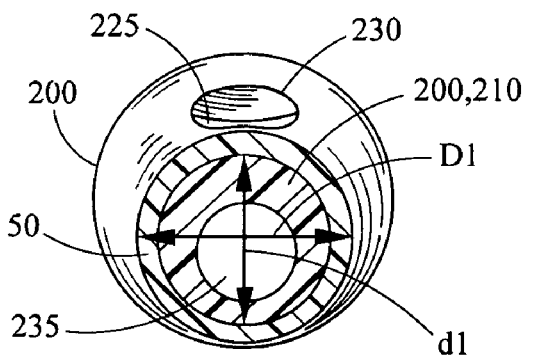
FIG. 7 is a cross-sectional view of the insert, according to one embodiment, taken along section 7-7 in FIG. 5.
Figure 8:
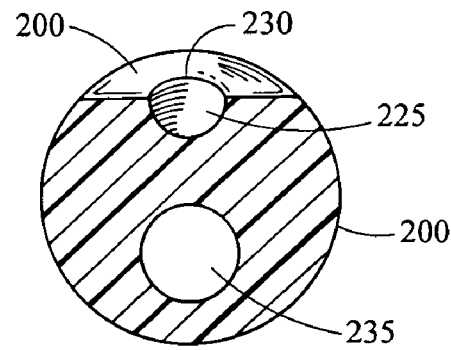
FIG. 8 is a cross-sectional view of the insert, according to one embodiment, taken along section 8-8 in FIG. 5.

As shown in FIGS. 5 and 6, the insert 200 has a first end 205 which includes a first operative coupling 210 for mechanically engaging the distal end of a first tube, for example, the outer sheath 50. The insert 200 also has a second end 215 which includes a second operative coupling 220 for mechanically engaging the proximal end of a second tube, for example, the outer guide channel member 80.

Referring now to FIG. 6, a first passageway 225 extends through the insert 150 from the second end 215 to an exit port 230 disposed on a surface of the insert 200 between the first operative coupling 210 and the second operative coupling 220. The first passageway 225 may be configured for slideably receiving a wire guide 16, as shown in FIGS. 4A and 4B. The first passageway 225 may flare radially outward toward the second end 215. This flaring may aid in ensuring a smooth entrance of the wire guide 16 when back-loaded into the delivery system 10, as described below. The first passageway 225 is in communication with the outer member channel 81 when the insert 200 is operatively coupled with the outer guide channel member 80, as shown in FIG. 6. The first passageway 225 may also be in communication with the inner member channel 71, as shown in FIG. 4A.

Figure 9:
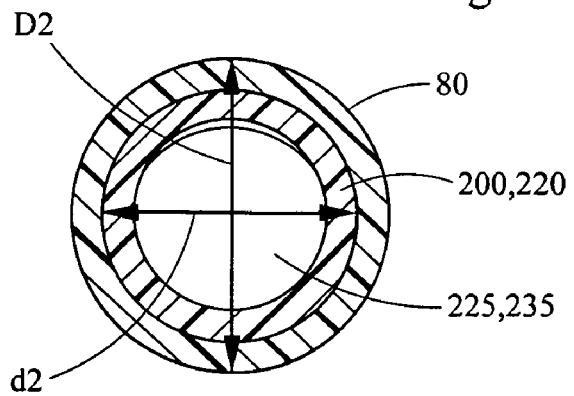
FIG. 9 is a cross-sectional view of the insert, according to one embodiment, taken along section 9-9 in FIG. 5.

A second passageway 235 may extend through the insert 150 from the first end 205 to the second end 215, according to one embodiment. The second passageway 235 passes through the first operative coupling 210 and the second operative coupling 220, as shown in FIGS. 6-9. In contrast, the first passageway 225 passes through the second operative coupling 220, but it does not pass through the first operative coupling 210. This is due to the origination of the first passageway 225 at the exit port 230 disposed between the first and second operative couplings 210, 220. The second operative coupling 220 includes both the first and second passageways, which may overlap with each other, as shown in FIGS. 6 and 9.

The first passageway 225 may be sized to accommodate or receive a wire guide 16 of a particular diameter, according to one embodiment. Alternatively, the first passageway 225 may be configured for receiving a catheter, cannula, or other medical device, tool, instrument, apparatus, or component of a particular size. In order to receive or accommodate a wire guide 16 (or other instrument) of a given diameter, the unflared portion of the first passageway 225 preferably may have a diameter of from about 0.001 inch to about 0.002 inch larger than the diameter of the wire guide 16 (or instrument) to be used. For example, to accommodate a first wire guide of 0.035 inch in nominal diameter, the first passageway 225 preferably may have a diameter of about 0.037 inch. In another example, to accommodate a second wire guide of 0.014 inch in nominal diameter, the first passageway 225 may have a diameter of about 0.016 inch.

Referring again to FIG. 6, a second passageway 235 may extend through the insert 150 from the first end 205 to the second end 215. According to one embodiment, the second passageway 235 may be configured for receiving the inner compression member 41, as shown in FIGS. 4A and 4B. Alternatively, the second passageway 235 may be configured for receiving a catheter, cannula, or other medical device, tool, instrument, apparatus, or component. In order to receive or accommodate an inner compression member 41 (or other instrument) of a particular diameter, the second passageway 225 preferably may have a diameter of from about 0.001 inch to about 0.002 inch larger than the diameter of the inner member 41 (or instrument). For example, if the inner compression member 41 has a diameter of approximately 0.016 inch, then the diameter of the second passageway 225 may be approximately 0.018 inch. If the instrument has a noncircular transverse cross-section, such as, for example, an elliptical, square, or rectangular cross-section, then the passageway may be sized according to the largest transverse dimension of the instrument.

According to one embodiment, the outer diameter d1 of the first operative coupling 210 is smaller than the outer diameter d2 of the second operative coupling 220. Consequently, the insert 200 may have a stepped profile when viewed along a plane passing through a centerline of the first and second passageways 225, 235, as shown in FIGS. 5-9. The difference between the outer diameter d1 of the first operative coupling 210 and the outer diameter d2 of the second operative coupling 220 may vary. For instance, the outer diameter d1 of the first operative coupling 210 may range from approximately 30% to approximately 90% of the outer diameter d2 of the second operative coupling 220. Alternatively, the outer diameter d1 of the first operative coupling 210 may range from about 60% to about 90% of the outer diameter d2 of the second operative coupling 220. According to one embodiment, the outer diameter d1 is about 80% of the outer diameter d2.

Similarly, when the insert 200 is operatively coupled with the outer sheath 50 and the outer member 80, the assembly may have a stepped profile as shown in FIGS. 5-9. According to one embodiment, the outer diameter D1 of the outer sheath 50 is smaller than the outer diameter D2 of the outer member 80. Having a smaller diameter outer sheath 50 may be an advantage in procedures involving narrow vessel passageways, endoscope working channels, or accessory channels for use with endoscopes. By way of example, the outer diameter D1 of the outer sheath 50 may range from approximately 30% to approximately 90% of the outer diameter D2 of the outer member 80. Alternatively, the outer diameter D1 of the outer sheath 50 may range from about 60% to about 90% of the outer diameter D2 of the outer member. According to one embodiment, the outer diameter of the outer sheath 50 is roughly 4 French, and the outer diameter of the outer member 80 is roughly 5 French.

According to one embodiment, a portion of the outer surface 250 of the insert 200 disposed between the outer sheath 50 and the outer member 80 may be substantially flush with a portion of the outer surface 255 of the outer sheath 50 and a portion of the outer surface 260 of the outer member 80, when the first and second operative couplings 210, 220 are mechanically engaged with the respective tubes. In other words, the flush portions are colinear. For example, as shown in FIG. 6, a bottom portion of the outer surface 250 of the insert 200 is substantially flush with a bottom portion of the outer surface 255 of the outer sheath 50 and a bottom portion of the outer surface 260 of the outer member 80. The term "bottom" is used for ease in describing the colinear portions of the outer surfaces (250, 255, and 260) of the insert 200, outer sheath 50, and outer member 80 as shown in FIG. 6, and is not intended to be limiting in terms of the positioning of the colinear portions. According to another embodiment, a portion of the outer surface 250 of the insert 200 may be flush with one of a portion of the outer surface 255 of the outer sheath 50 and a portion of the outer surface 260 of the outer member 80. Alternatively, there may be no colinearity among portions of the surfaces of the insert 200, outer sheath 50 and outer member 80.

Preferably, the exit port 230 of the first passageway 225 is disposed at an angle of greater than zero with respect to a longitudinal axis of the insert 200. In this configuration, which may be referred to as a breech position opening or breech configuration, the exit port 230 opens in the direction of the outer surface of the outer sheath 50. The breech configuration of the exit port 230 is facilitated by the stepped profile of the insert 200, as described above. As shown in FIG. 6, the exit port 230 may be disposed at an acute angle with respect to the longitudinal axis of the insert. In other words, the exit port 230 may be disposed at an angle in the range of from about 1 degree to less than about 90 degrees with respect to a longitudinal axis of the insert. For example, the exit port 230 may be disposed at an angle in the range of from about 5 degrees to about 45 degrees. In another example, the exit port 230 may be disposed at an angle in the range of from about 10 degrees to about 30 degrees. According to one embodiment, the angle at which the exit port 230 is disposed with respect to the longitudinal axis of the insert 200 is approximately 20 degrees. The exit port 230 shown in FIG. 6 has a substantially linear cross section; however, the exit port 230 may alternatively have a curved cross section, such as, for example, a concave cross section.

The exit port 230 may be used, for example, for front-loading and/or back-loading a wire guide 16. In a back-loading procedure for a delivery system 10 having a breech position opening as described above, the wire guide 16 may enter the first passageway 225 of the insert 200 from the second end 215, pass through the first passageway 225 in a proximal direction, and exit the insert 200 through the exit port 230. Conversely, in a front-loading procedure for a delivery system 10 having a breech position opening, the physician may feed the wire guide 16 into the exit port 230 from a proximal direction. In this case, the wire guide 16 may traverse the first passageway 225 in a distal direction, and then exit from the second end 215 of the insert 200. In either of these scenarios, the wire guide 16 may avoid making sharp turns away from the longitudinal axis of the insert 200 that may result in kinking of the wire guide 16.

The overall axial length of the exit port 230 (in other words, the length spanned by the exit port 230 in a longitudinal direction) may vary. In one embodiment, the length spanned by the exit port 230 ranges from about 0.1 mm to about 4.0 mm. Another embodiment has a length of approximately 1.0 mm. The overall width of the exit port 230 may also vary. For example, the width of the exit port 230 ranges from about 1 French to about 4 French (approximately 0.33 mm to approximately 1.32 mm). In another example, the width of the exit port 230 may be the approximate difference between the outer diameter D2 of the second end 215 of the insert 200 and the outer diameter D1 of the first end 205 of the insert 200.

The length of the insert 200 between the first operative coupling 210 and the second operative coupling 220 may range from approximately 0.25 mm to approximately 5 mm, according to one embodiment. Preferably, the length is sufficient to accommodate the exit port 230 as described above, but is short enough to avoid the formation of a potential kink site or a detrimentally stiff region between the coupled tubes. Preferably, the length from the first operative coupling 210 to the second operative coupling 220 may range from about 0.5 mm to about 3 mm. According to one embodiment, the length between the first operative coupling 210 and the second operative coupling 220 is about 2.0 mm. According to an alternative embodiment, the length of the insert 200 between the first operative coupling 210 and the second operative coupling 220 is about 1.5 mm.

The insert 200 may be formed of any biocompatible material, such as, for example, one or more polymeric or metallic materials. Suitable materials include polyamides (e.g., Nylon), elastomers, fluorocarbons (e.g., polytetrafluoroethylene (PTFE) or fluoroethylene-propylene (FEP)), polyether block amide (PEBA), polyolefins, polyimides, polyurethanes, polyvinyl chloride (PVC), stainless steel, nickel, titanium, nickel-titanium, Nitinol, platinum, palladium, gold, tantalum and/or tungsten. The insert 200 may be fabricated by casting methods known in the art. Preferably, the insert 200 material may be selected so that the insert 200 has mechanical properties (e.g., stiffness, hardness, torsional rigidity) which are similar to those of one or both of the tubes (e.g., the outer sheath 50 and the outer member 80) to which it is operatively coupled.

According to one embodiment, the first end 205 of the insert 200 is disposed within the distal end 58 of the outer sheath 50 when the first operative coupling 210 is mechanically engaged with the outer sheath 50, as shown in FIG. 6. Consequently, the first operative coupling 210 has an outer diameter d1 configured to fit within the inner diameter D1' of the outer sheath 50. According to another embodiment, however, the distal end 58 of the outer sheath 50 may be disposed within the first end 205 of the insert 200 when the first operative coupling 210 is mechanically engaged with the outer sheath 50. In this case, the outer sheath 50 has an outer diameter D1 that is configured to fit within the inner diameter d1' of the first operative coupling 210.

According to another embodiment, when the second operative coupling 220 is mechanically engaged with the outer member 80, the second end 215 of the insert 200 is disposed within the proximal end 88 of the outer member 80. Consequently, the second operative coupling 220 has an outer diameter d2 configured to fit within the inner diameter D2' of the outer member 80. According to another embodiment, however, the proximal end of the outer member 80 may be disposed within the second end 215 of the insert 200 when the second operative coupling 220 is mechanically engaged with the outer member 80. In this case, the outer member 80 has an outer diameter D2 that is configured to fit within the inner diameter d2' of the second operative coupling 220.

The length of the first operative coupling 210 may be in the range of from about its outer diameter D1 to about 2.5 times its outer diameter D1. Preferably, the length of the first operative coupling 210 is in the range of from about 1.5 times its outer diameter D1 to about 2.0 times its outer diameter D1. According to one embodiment, the length of the first operative coupling 210 is about 1.75 times its outer diameter D1.

The length of the second operative coupling 220 may be in the range of from about its outer diameter D2 to about 2.5 times its outer diameter D2. For example, the length of the second operative coupling 220 may be in the range of from about 1.5 times its outer diameter D2 to about 2.0 times its outer diameter D2. According to one embodiment, the length of the second operative coupling 220 is about 1.75 times its outer diameter D2.

The first operative coupling 210 includes one or more engagement elements 240 that protrude from a surface, such as its external surface 242, according to one embodiment. The one or more engagement elements 240 are mechanically associated with a wall of the outer sheath 50 when the first operative coupling 210 is engaged with the outer sheath 50. As used herein, the terms "mechanically associated with" or "mechanically associating with" include at least one of engaging, contacting, pressing against, deforming, and penetrating.

The second operative coupling 220 includes one or more engagement elements 240 that protrude from a surface, such as its external surface 244, according to one embodiment. The one or more engagement elements 240 are mechanically associated with a wall of the outer member 80 when the second operative coupling 220 is engaged with the outer member 80. As above, the terms "mechanically associated with" or "mechanically associating with" include at least one of engaging, contacting, pressing against, deforming, and penetrating.

The engagement elements 240 may be threads 246, according to one embodiment. Preferably, the threads have a helical configuration and extend substantially continuously about the circumference of the first and/or second operative coupling 210, 220. The threads 246 may have any profile known in the art suitable for mechanically associating with the wall of a tube, such as the outer sheath 50 or the outer member 80; For example, the threads 246 may have a generally V-shaped profile 246a, as shown in FIGS. 6 and 10. Alternatively, the threads 246 may have a generally square-shaped profile 246b with substantially parallel sides, as shown in FIG. 11. The threads 246 may be formed of a biocompatible metallic material (e.g., stainless steel, nickel-titanium, Nitinol, etc.) or a polymer, such as, for example, Nylon.

The threads 246 may be integrally formed with the first and/or the second operative coupling 210, 220, according to one embodiment. For example, and as shown in FIGS. 10 and 11, threads 246 may be disposed on an external surface 242 of the first second operative coupling 210 such that the external threads may mechanically associate with the inner wall of the tube. According to this embodiment, the inner wall of the tube which receives the threaded coupling may include internal threads with a pitch substantially corresponding to the pitch of the external threads on the coupling. Alternatively, the inner wall of the tube may not include threads, but rather may be substantially smooth. In one embodiment the wall of the tube may include a reinforcement structure 43 having spacings 43' that substantially coincide with the pitch of the threads 240a, as will be further described below.

According to another embodiment, threads 246 may be disposed on an internal surface of the first and/or the second operative coupling 210, 220, such that the internal threads (not shown in the figures) may mechanically associate with the outer wall of the tube. According to this embodiment, the outer wall of the tube may include external threads with a pitch substantially corresponding to the pitch of the internal threads on the coupling. Alternatively, the outer wall of the tube may not include threads, but rather may be substantially smooth. In one embodiment the wall of the tube may include a reinforcement structure having spacings that substantially coincide with the pitch of the threads, as will be further described below.

Alternatively, the threads 246 may be formed as part of a separate unit, e.g., a threaded fitting 246', which may be secured to the first operative coupling 210 and/or the second operative coupling 220 of the insert 200. According to this embodiment, the first operative coupling 210 may be a two-piece assembly which includes the threaded fitting 246', as shown for example in FIG. 12. According to another embodiment, the second operative coupling 220 may be a two-piece assembly which includes a threaded fitting 246'. The threaded fitting 246' may be secured to the first and/or second operative couplings 210, 220 by any coupling method known in the art. Preferably, the threaded fitting 246' may be formed of a biocompatible metallic material (e.g., stainless steel, nickel-titanium, etc.). Alternatively, the threaded fitting 246' may be made of a polymer. Suitable threaded fittings 246' may be obtained from commercial sources, such as, for example, Emhart Teknologies (Shelton, Conn.), which markets Heli-Coil® Screw Thread Inserts.

In use, the threaded fitting 246' may be first engaged with the first or second operative coupling 210, 220 and then engaged with the respective tube (e.g., the outer sheath 50 or outer member 80), according to one embodiment. Alternatively, according to another embodiment, the threaded fitting 246' may be first engaged with the outer sheath 50 or outer member 80, and then engaged with the respective first or second operative coupling 210, 220.

Figure 14:
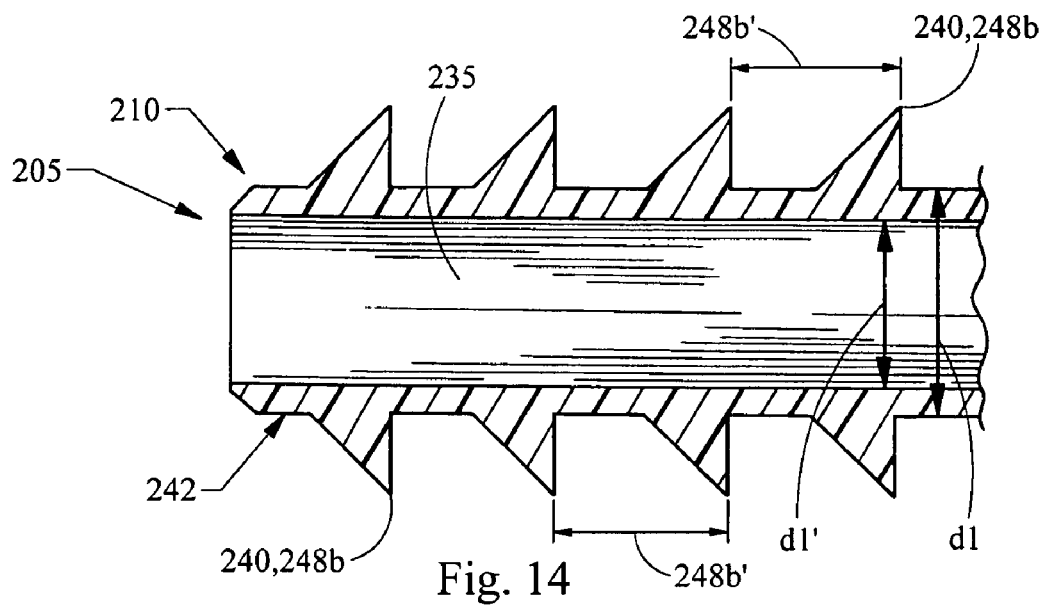
FIG. 14 is a longitudinally sectioned view of an operative coupling including barbs according to another embodiment.

According to another embodiment, the engagement elements 240 may be barbs 248. For example, one or more barbs 248 may be disposed on an external surface 242 of the first operative coupling 210, as shown in FIGS. 13 and 14. The barbs 248 may have any profile known in the art which is suitable for mechanically associating with the inner wall of a tube, such as the outer sheath 50 or the outer member 80. For example, the barbs 248 may have the profile 248a shown in FIG. 13, in which the barbs 248 are consecutively arranged, or the barbs 248 may have the profile 248b shown in FIG. 14, in which the barbs 248 are separated by spacings.

According to one embodiment, a barb 248 may be disposed about the entire circumference of the respective coupling. Alternatively, a barb 248 may be disposed about only a portion of the circumference of the respective coupling. The barbs 248 may be formed of a biocompatible metallic material (e.g., stainless steel, nickel-titanium, Nitinol, etc.) or a polymer, such as, for example, Nylon. According to one embodiment, the barbs 248 may be deployable; that is, they may expand from a collapsed or low profile configuration to a protruded configuration to mechanically associate with the wall of the tube.

The barbs 248 may be integrally formed with the first operative coupling 210 and/or the second operative coupling 220, according to one embodiment. Alternatively, the barbs 248 may be formed as part of a separate unit, e.g., a barbed fitting 248', which may be secured to the first and/or second operative couplings 210, 220. According to this embodiment, the first operative coupling 210 may be a two-piece assembly which includes the barbed fitting 248'. The second operative coupling 220 may also be a two-piece assembly which includes the barbed fitting 248'. The barbed fitting 248' may be secured to the first and/or second operative couplings 210, 220 by any coupling method known in the art. Such barbed fittings 248' preferably may be formed of a biocompatible metallic material (e.g., stainless steel, nickel-titanium, etc.). Alternatively, the barbed fitting 248' may be made of a polymer. Suitable barbed fittings 248' may be obtained from commercial sources, such as, for example, Parker Hannifin (Cleveland, Ohio).

In use, the barbed fitting 248' may be first engaged with the first or second operative coupling 210, 220 and then engaged with the respective tube (e.g., the outer sheath 50 or outer member 80), according to one embodiment. Alternatively, according to another embodiment, the barbed fitting 248' may be first engaged with the outer sheath 50 or outer member 80, and then engaged with the respective first or second operative coupling 210, 220.

According to an embodiment in which a wall of the outer sheath 50 includes a reinforcement structure 43 having spacings 43' between constituents thereof, as described previously, the pitch or spacing of the engagement elements 240 of the first operative coupling 210 may be selected to substantially coincide with the spacings 43' of the reinforcement structure 43. Alternatively, a multiple of the pitch or spacing of the engagement elements 240 of the first operative coupling 210 may be selected to substantially coincide with the spacings 43' of the reinforcement structure 43.

Figure 15:
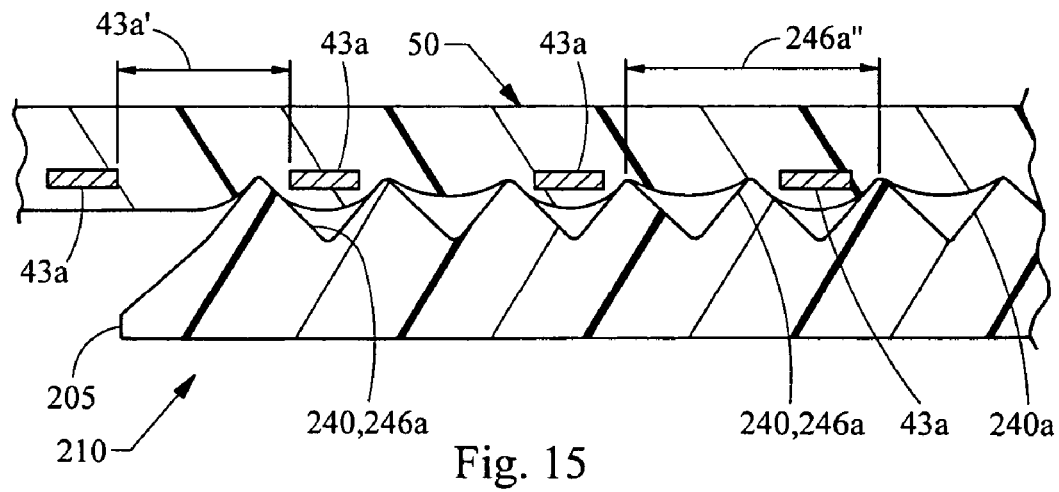
FIG. 15 is a longitudinally sectioned view of threads of an operative coupling mechanically associated with a reinforcement structure in a tube wall, according to one embodiment.
Figure 16:
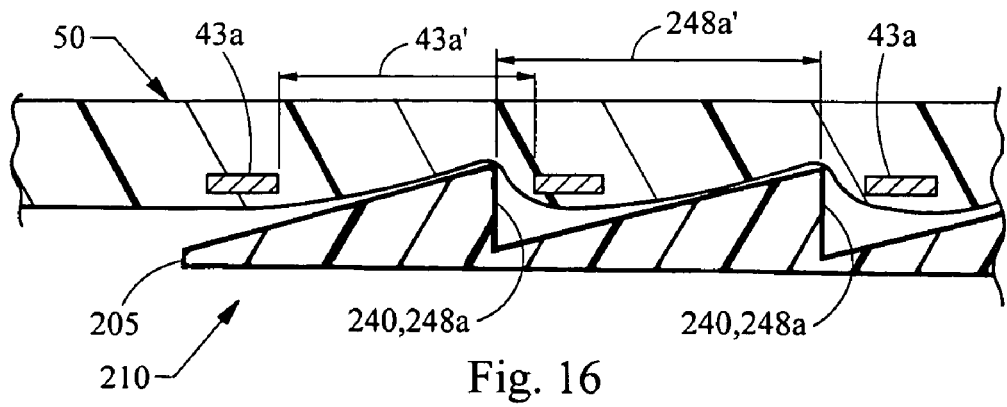
FIG. 16 is a longitudinally sectioned view of barbs of an operative coupling mechanically associated with a reinforcement structure in a tube wall, according to another embodiment.

For example, if the first operative coupling 210 includes threads 246 having a substantially V-shaped profile 246a, a multiple of the pitch 246a" of the threads 246 may be designed to substantially coincide with the spacings 43' of the reinforcement structure 43, as shown in FIG. 15. In another example, if the first operative coupling 210 includes barbs 248, the pitch 248a' of the barbs 248 may be designed to substantially coincide with the spacings 43' of the reinforcement structure 43, as shown in FIG. 16. According to these embodiments, when the first operative coupling 210 is engaged with the outer sheath 50, the engagement elements 240 (e.g., threads 246 or barbs 248) of the first operative coupling 210 may reside within at least a portion of the spacings 43'.

For example, the reinforcement structure 43 may be a coil having a helical configuration extending from the distal end 58 of the outer sheath 50 along at least a portion of the length of the tube. As discussed previously, such a coil may be a flat wire coil (43a), as shown in FIG. 3A, or a round wire coil (43b), as shown in FIG. 3B. Due to the helical configuration, the reinforcement structure 43 includes a plurality of turns in a circumferential direction, with spacings 43' between the turns. As shown, for example, in FIG. 15, a first operative coupling 210 having threads 246 with a generally V-shaped profile 246a may be designed such that the threads 246 reside within a portion of the spacings 43' of the helical reinforcement structure 43 when the coupling 210 is engaged with the outer sheath 50. It may be desirable for the threads 246 to deform or penetrate the wall of the tube in order to attain this interlocked configuration.

Alternatively, a first operative coupling 210 having external threads 246 with a generally square-shaped profile 246b and substantially parallel sides may be adapted such that the threads 246 reside within the spacings 43' of the helical reinforcement structure 43 when the coupling 210 is engaged with the outer sheath 50. Similarly, barbs 248 may be used as the engagement elements 240 of the first operative coupling 210, and the configuration and spacing 248a' of the barbs 248 may be designed such that the barbs 248 reside within a portion of the spacings 43' of the helical reinforcement structure 43 when the first operative coupling 210 is engaged with the outer sheath 50, as shown in FIG. 16. As in the previous example, it may be necessary for the threads 246 or the barbs 248 to deform or penetrate the wall of the tube in order to attain this interlocked configuration.

According to an embodiment in which a wall of the outer member 80 includes a reinforcement structure 43 having spacings 43' between constituents thereof, as described previously, the pitch or the spacing—or a multiple of the pitch or the spacing—of the engagement elements 240 of the second operative coupling 220 may be selected to substantially coincide with the spacings 43' of the reinforcement structure 43.

For example, if the second operative coupling 220 includes threads 246 having a generally V-shaped profile 246a, a multiple of the pitch 246a" of the threads 246 may be designed to substantially coincide with the spacings 43' of the reinforcement structure 43. When the second operative coupling 220 is engaged with the outer member 80, the threads 246 of the second operative coupling 220 may reside within at least a portion of the spacings 43', according to this embodiment. Alternatively, if barbs 248 are used as the engagement elements of the second operative coupling 220, the spacing 248a' between barbs 248 may be selected to substantially coincide with the spacings 43' of the reinforcement structure 43. Consequently, the barbs 248 may reside within at least a portion of the spacings 43' when the second operative coupling 220 is engaged with the outer member 80.

For example, the reinforcement structure 43 may be a coil having a helical configuration extending from the proximal end 88 of the outer member 80 along at least a portion of the length of the tube. Due to the helical configuration, the reinforcement structure 43 includes a plurality of turns in a circumferential direction, with spacings 43' between the turns. A second operative coupling 220 having threads 246 with a generally V-shaped profile 246a, for example, may be adapted such that the threads 246 reside within the spacings 43' of the helical reinforcement structure 43 when the coupling 220 is engaged with the outer member 80. It may be necessary for the threads 246 to deform or penetrate the wall of the tube in order to attain this interlocked configuration.

Alternatively, a second operative coupling 220 having threads 246' with a generally square-shaped profile 246b and substantially parallel sides may be adapted such that the threads 246 reside within the spacings 43' of the helical reinforcement structure 43 when the coupling 220 is engaged with the outer member 80. Similarly, barbs 248 may be used as the engagement elements 240 of the second operative coupling 220, and the configuration and spacing of the barbs 248 may be designed such that the barbs 248 reside within a portion of the spacings 43' of the helical reinforcement structure 43 when the second operative coupling 220 is engaged with the outer member 80. As in the previous example, it may be desirable for the threads 246 or the barbs 248 to deform or penetrate the wall of the tube in order to attain this interlocked configuration.

An interlocked configuration including the engagement elements 240 of the first operative coupling 210 and the reinforcement structure 43 of the outer sheath 50 may be obtained with engagement elements 240 other than the threads 246 or the barbs 248 described above. Any engagement elements 240 that protrude from a surface of the first operative coupling 210 and have a spacing that substantially matches the spacing 43' of the reinforcement structure 43 may be used. Similarly, an interlocked configuration including the engagement elements 240 of the second operative coupling 220 and the reinforcement structure 43 of the outer member 80 may be obtained with engagement elements 240 other than the threads 246 and the barbs 248 described above. Any engagement elements 240 that protrude from a surface of the second operative coupling 220 and have a spacing that substantially matches the spacing 43' of the reinforcement structure 43 may be used.

For example, if the reinforcement structure 43 comprises a mesh or a braid, an interlocked configuration may be obtained with an arrangement of discrete barbs, prongs, or other protruding elements. Such engagement elements 240 may be deployable; that is, they may expand from a collapsed or low profile configuration to a protruded configuration to mechanically associate with the wall of the tube.

A method of assembling a catheter is included as part of this disclosure. The method includes the steps of providing a first tube (such as the outer sheath 50 described previously), providing a second tube (such as the outer guide channel member 80 described previously), and providing an insert 200. The insert 200 has, at a first end 205, a first operative coupling 210 for engaging the outer sheath 50 at its distal end. At a second end 215, the insert 200 has a second operative coupling 220 for engaging the outer member 80 at its proximal end. The insert also includes a first passageway 225 extending through the insert 200 from the second end 215 to an exit port 230 disposed between the first operative coupling 210 and the second operative coupling 220. Next, the method includes engaging the first operative coupling 210 with the outer sheath 50 at its distal end, and engaging the second operative coupling 220 with the outer member 80 at its proximal end. The engaging of the tubes with the respective couplings may be done in either order or simultaneously.

The step of engaging the first operative coupling 210 with the outer sheath 50 may include, according to one embodiment, a step of mechanically associating one or more engagement elements 240 of the first operative coupling 210 with a wall of the outer sheath 50. Similarly, the step of engaging the second operative coupling 220 with the outer member 80 may include a step of mechanically associating one or more engagement elements 240 of the second operative coupling 220 with a wall of the outer member 80. The step of mechanically associating includes at least one of engaging, contacting, pressing against, deforming, and penetrating.

According to another embodiment, the wall of the outer sheath 50 may include a reinforcement structure 43 having spacings 43' between constituents thereof. In this case, the step of mechanically associating may further include disposing the one or more engagement elements 240 of the first operative coupling 210 within at least a portion of the spacings 43' of the reinforcement structure 43.

Similarly, a wall of the outer member 80 may include a reinforcement structure 43 having spacings 43' between constituents thereof, and the step of mechanically associating may further include disposing the one or more engagement elements 240 of the second operative coupling 220 within at least a portion of the spacings 43' of the reinforcement structure 43'.

Although the present invention has been described with reference to certain embodiments thereof, other embodiments are possible without departing from the present invention. The spirit and scope of the appended claims should not be limited, therefore, to the description of the preferred embodiments contained herein. All devices and methods that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

The invention claimed is:

1. An insert for joining sheaths for use in a medical device, the insert comprising:
   a tubular body having a first end including a first operative coupling for engaging a first tube at a distal end thereof and a second end including a second operative coupling for engaging a second tube at a proximal end thereof, an inner diameter d1' of the first operative coupling being smaller than an inner diameter d2' of the second operative coupling, and an outer diameter d1 of the first operative coupling being smaller than an outer diameter d2 of the second operative coupling; and
   a first passageway extending through the tubular body from the second end to an exit port located directly on the tubular body between the first operative coupling and the second operative coupling,
   a second passageway extending through the tubular body from the first end to the second end, the first and second passageways overlapping with each other so as to be in fluid communication,
   wherein the exit port is an opening disposed at an angle of greater than zero with respect to a longitudinal axis of the tubular body, the exit port thereby having a breech configuration.

2. The insert according to claim 1, wherein the first operative coupling and the second operative coupling comprise one or more engagement elements that protrude from a surface thereof.

3. The insert according to claim 2, wherein the one or more engagement elements include at least one of threads and barbs.

4. The insert according to claim 2, wherein the one or more engagement elements are integrally formed with at least one of the first operative coupling and the second operative coupling.

5. The insert according to claim 1, wherein the angle of greater than zero is an acute angle.

6. The insert according to claim 2, further comprising a first tube engaged with the first operative coupling so that one or more engagement elements of the first operative coupling mechanically associate with a wall of the first tube, wherein mechanically associating with comprises at least one of contacting, pressing against, deforming, and penetrating.

7. The insert according to claim 2, further comprising a second tube engaged with the second operative coupling so that one or more engagement elements of the second operative coupling mechanically associate with a wall of the second tube, wherein mechanically associating with comprises at least one of contacting, pressing against, deforming, and penetrating.

8. The insert according to claim 6, wherein the wall of the first tube comprises a first reinforcement structure having spacings between constituents thereof, and the one or more engagement elements of the first operative coupling reside within at least a portion of the spacings.

9. The insert according to claim 7, wherein the wall of the second tube includes a second reinforcement structure having spacings between constituents thereof, and the one or more engagement elements of the second operative coupling reside within at least a portion of the spacings.

10. A catheter comprising:
    a first tube;
    a second tube;
    an insert comprising a tubular body having a first end and a second end, the first end including a first operative coupling engaged to a distal end of the first tube, the second end including a second operative coupling engaged to a proximal end of the second tube, an inner diameter d1' of the first operative coupling being smaller than an inner diameter d2' of the second operative coupling and an outer diameter d1 of the first operative coupling being smaller than an outer diameter d2 of the second operative coupling, the tubular body comprising a first passageway extending therethrough from the second end to an exit port located directly on the tubular body between the first operative coupling and the second operative coupling and further comprising a second passageway extending therethrough from the first end to the second end, the first and second passageways overlapping with each other so as to be in fluid communication, wherein the exit port is an opening disposed at an angle of greater than zero with respect to a longitudinal axis of the tubular body, the exit port thereby having a breech configuration.

11. The catheter according to claim 10, wherein the first operative coupling and the second operative coupling each comprise one or more engagement elements that protrude from a respective surface thereof.

12. The catheter according to claim 11, wherein the one or more engagement elements are integrally formed with at least one of the first operative coupling and the second operative coupling.

13. The catheter according to claim 10, wherein the angle of greater than zero is an acute angle.

14. The catheter according to claim 10, wherein the first end of the insert is disposed within the distal end of the first tube and the second end of the insert is disposed within the proximal end of the second tube.

15. The catheter according to claim 11, wherein the first tube comprises a first reinforcement structure disposed within a wall of the first tube, the first reinforcement structure having spacings between constituents thereof, and
wherein the one or more engagement elements of the first operative coupling reside within at least a portion of the spacings.

16. The catheter according to claim 15, wherein the first reinforcement structure comprises a helical configuration extending along a length of the first tube from the distal end and forming a plurality of turns in a circumferential direction, with the spacings between the turns.

17. The catheter according to claim 11, wherein the second tube comprises a second reinforcement structure disposed within a wall of the second tube, the second reinforcement structure having spacings between constituents thereof, and
wherein the one or more engagement elements of the second operative coupling reside within at least a portion of the spacings.

18. The catheter according to claim 17, wherein the second reinforcement structure comprises a helical configuration extending along a length of the second tube from the proximal end and forming a plurality of turns in a circumferential direction, with the spacings between the turns.

19. A method of assembling a catheter comprising the steps of:
providing a first tube;
providing a second tube;
providing an insert comprising a tubular body having a first end including a first operative coupling and a second end including a second operative coupling, an inner diameter d1' of the first operative coupling being smaller than an inner diameter d2' of the second operative coupling and an outer diameter d1 of the first operative coupling being smaller than an outer diameter d2 of the second operative coupling, wherein the tubular body includes a first passageway extending therethrough from the second end to an exit port disposed directly on the tubular body between the first operative coupling and the second operative coupling, the exit port being an opening disposed at an angle of greater than zero with respect to a longitudinal axis of the tubular body, the exit port thereby having a breech configuration, and wherein the tubular body includes a second passageway extending therethrough from the first end to the second end, the first and second passageways overlapping with each other so as to be in fluid communication;
engaging the first operative coupling with a distal end of the first tube; and
engaging the second operative coupling with a proximal end of the second tube.

20. The method of claim 19, wherein the step of engaging the first operative coupling with the first tube comprises a step of mechanically associating one or more engagement elements of the first operative coupling with a wall of the first tube, and the step of engaging the second operative coupling with the second tube comprises a step of mechanically associating one or more engagement elements of the second operative coupling with a wall of the second tube,
wherein the step of mechanically associating includes at least one of contacting, pressing against, deforming, and penetrating.

21. The method of claim 20, wherein a wall of the first tube comprises a first reinforcement structure having spacings between constituents thereof, and the step of mechanically associating further comprises disposing the one or more engagement elements of the first operative coupling within at least a portion of the spacings of the first reinforcement structure.

22. The method of claim 20, wherein a wall of the second tube comprises a second reinforcement structure having spacings between constituents thereof, and the step of mechanically associating further comprises disposing the one or more engagement elements of the second operative coupling within at least a portion of the spacings of the second reinforcement structure.

23. The insert of claim 1, wherein the outer diameter of the first operative coupling ranges from about 30% to about 90% of the outer diameter of the second operative coupling.

24. The insert of claim 23, wherein the outer diameter of the first operative coupling ranges from about 60% to about 90% of the outer diameter of the second operative coupling.

25. The insert of claim 1, wherein the insert has a stepped profile when viewed along a plane passing through a centerline thereof.

26. The insert of claim 1, wherein the first passageway flares radially outward toward the second end, the first passageway having a nonconstant diameter along a length thereof.

27. The insert of claim 1, wherein a length of the insert between the first operative coupling and the second operative coupling is in the range of from about 0.25 mm to about 5 mm.

28. The catheter of claim 10, wherein a portion of an outer surface of the tubular body is substantially flush with a portion of an outer surface of the first tube and with a portion of an outer surface of the second tube, the portions of the outer surfaces being colinear.

29. The method of claim 19, wherein, after engaging the first operative coupling with the distal end of the first tube and after engaging the second operative coupling with the proximal end of the second tube, a portion of an outer surface of the tubular body is substantially flush with a portion of an outer surface of the first tube and with a portion of an outer surface of the second tube, the portions of the outer surfaces being colinear.

30. The method of claim 19, wherein engaging the first operative coupling with the distal end of the first tube comprising disposing the first end of the insert within the distal end of the first tube, and wherein engaging the second operative coupling with the proximal end of the second tube comprises disposing the second end of the insert within the proximal end of the second tube.

* * * * *